(12) United States Patent
Durocher et al.

(10) Patent No.: US 10,421,950 B2
(45) Date of Patent: *Sep. 24, 2019

(54) ENHANCED PRODUCTION OF RECOMBINANT PROTEINS BY TRANSIENT TRANSFECTION OF SUSPENSION-GROWING MAMMALIAN CELLS

(75) Inventors: Yves Durocher, Montreal (CA); Sylvie Perret, Montreal (CA); Phuong Lan Pham, Laval (CA); Amine A. Kamen, Montreal (CA)

(73) Assignee: NATIONAL RESEARCH COUNCIL OF CANADA (CA)

( * ) Notice: Subject to any disclaimer, the term of this patent is extended or adjusted under 35 U.S.C. 154(b) by 2449 days.

This patent is subject to a terminal disclaimer.

(21) Appl. No.: 10/477,148

(22) PCT Filed: May 7, 2002

(86) PCT No.: PCT/CA02/00683
§ 371 (c)(1),
(2), (4) Date: Jul. 22, 2004

(87) PCT Pub. No.: WO02/090533
PCT Pub. Date: Nov. 14, 2002

(65) Prior Publication Data
US 2005/0170450 A1    Aug. 4, 2005

Related U.S. Application Data

(60) Provisional application No. 60/288,790, filed on May 7, 2001.

(51) Int. Cl.
| | | |
|---|---|---|
| *C12N 15/85* | (2006.01) | |
| *C12N 15/11* | (2006.01) | |
| *C12N 15/113* | (2010.01) | |
| *C12N 15/63* | (2006.01) | |
| *C12N 5/071* | (2010.01) | |
| *C12P 21/02* | (2006.01) | |

(52) U.S. Cl.
CPC .......... *C12N 5/0686* (2013.01); *C12N 15/85* (2013.01); *C12P 21/02* (2013.01); *C12N 2500/90* (2013.01); *C12N 2510/02* (2013.01); *C12N 2800/108* (2013.01); *C12N 2840/20* (2013.01); *C12N 2840/203* (2013.01); *C12N 2840/44* (2013.01)

(58) Field of Classification Search
None
See application file for complete search history.

(56) References Cited

U.S. PATENT DOCUMENTS

| | | | |
|---|---|---|---|
| 5,024,939 A | | 6/1991 | Gorman |
| 5,024,947 A | | 6/1991 | Inlow et al. |
| 5,707,830 A | * | 1/1998 | Calos .......................... 435/69.1 |
| 5,804,374 A | * | 9/1998 | Baltimore ............ C12Q 1/6897 435/6.13 |
| 5,854,004 A | * | 12/1998 | Czernilofsky et al. ....... 435/7.21 |
| 5,879,919 A | | 3/1999 | Grinnell |
| 6,133,025 A | * | 10/2000 | Seed ..................... C07K 14/005 435/320.1 |
| 6,210,922 B1 | | 4/2001 | Kamen et al. |
| 2003/0059942 A1 | * | 3/2003 | Cho et al. ..................... 435/456 |

FOREIGN PATENT DOCUMENTS

WO        9837185 A       8/1998

OTHER PUBLICATIONS

Massie et al, Inducible Overexpression of a Toxic Protein by an Adenovirus Vector with a Tetracycline-Regulatable Expression Cassette, Journal of Virology, Mar. 1998, p. 2289-2296.*
Shirakata and Hirai, Identification of Minimal oriP of Epstein-Barr Virus Requried for DNA Replication, J. Biochem, 1998, pp. 175-181.*
LaÖNgle-Rouault et al,. Up to 100-Fold Increase of Apparent Gene Expression in the Presence of Epstein-Barr Virus oriP Sequences and EBNA1: Implications of the Nuclear Import of Plasmids, Journal of Virology, Jul. 1998, p. 6181-6185.*

(Continued)

*Primary Examiner* — Maria Marvich
(74) *Attorney, Agent, or Firm* — Cermak Nakajima & McGowan LLP; Shelly Guest Cermak

(57) ABSTRACT

Disclosed is a new process for the production of recombinant proteins, by transient transfection of suspension-grown human embryonic kidney cells (293 cell line and its genetic variants) with an expression vector, using polyethylenimine (PEI) as a transfection reagent. In a preferred embodiment, the process uses 293E cells expressing the Epstein-Barr virus (EBV) EBNA 1 protein, in combination with an oriP-based episomal expression vector having an improved cytomegalovirus expression cassette comprising the CMV5 promoter. The process combines in a single step the cell growth, transfection and protein expression, is carried out without changing the culture medium, and allows to achieve high expression levels in a short period of time. The process may be carried out in a serum-free, low-protein culture medium, is easily scalable, compatible with continuous production processes, and fully adapted to high-throughput production of milligram quantities of recombinant proteins.

11 Claims, 18 Drawing Sheets
Specification includes a Sequence Listing.

(56) References Cited

OTHER PUBLICATIONS

Geoffroy et al, A PEBP2a/AML-1-related Factor Increases Osteocalcin Promoter Activity through Its Binding to an Osteoblast-specific cis-Acting Element, JBC, 1995, pp. 30973-30979.*

Massie et al., "New adenovirus vectors for protein production and gene transfer", *Cytotechnology* 28, 1998, pp. 53-64.

Boussif et al., "A versatile vector for gene and oligonucleotide transfer into cells in culture and in vivo: Polyethylenimine", *Proc. National Academy of Science USA*, vol. 92, Aug. 1995, pp. 7297-7301.

Schlaeger et al., "Transient gene expression in mammalian cells grown in serum-free suspension culture", *Cytotechnology* 30, 1999, pp. 71-83.

Wurm et al., "Large-scale transient expression in mammalian cells for recombinant protein production", http//biomednet.com/elecref/0958166901000156, *Current Opinion in Biotechnology*, 1999, 10, pp. 156-159.

Gahn et al., "An EBNA-1-Dependent Enhancer Acts from a Distance of 10 Kilobase Pairs to Increase Expression of the Epstein-Barr Virus LMP Gene", *Journal of Virology*, Apr. 1995, pp. 2633-2636.

Yates et al., "Stable replication of plasmids derived from Epstein-Barr virus in various mammalian cells", *Nature*, vol. 313, Feb. 28, 1985, pp. 812-815.

Tanaka et al., "Construction of Epstein-Barr Virus-Based Expression Vector Containing Mini-OriP", *Biochemical and Biophysical Research Communications*, 294, 1999, pp. 938-943.

Ca Chianes et al "Epstein-Barr Virus-Derived Vectors for Transient and Stable Expression of Recombinant Proteins", *Biotechniques*, vol. 15, No. 2, 1993.

Wu et al., "Separation of the DNA Replication, Segregation, and Transcriptional Activation Functions of Epstein-Barr Nuclear Antigen 1", *Journal of Virology*, Mar. 2002, pp. 2480-2490.

Van Craenenbroeck et al., "Episomal vectors for gene expression in mammalian cells", *Eur. Journal of Biochemistry*, 267, 2000, pp. 5665-5678.

Middleton et al., "Retention of Plasmid DNA in Mammalian Cells is Enhanced by Binding of the Epstein-Barr Virus Replication Protein EBNA1", *Journal of Virology*, Jun. 1994, pp. 4067-4071.

Langle-Rouault et al., "Up to 100-Fold Increase of Apparent Gene Expression in the Presende of Epstein-Barr Virus oriP Sequences and EBNA1: Implications of the Nuclear Import of Plasmids", *Journal of Virology*, Jul. 1998, pp. 6181-6185.

Wysokenski et al., Multiple EBNA1-Binding Sites Are Required to Form an EBNA1-Dependent Enhancer and to Activate a Minimal Replicative Origin within oriP of Epstein-Barr Virus, *Journal of Virology*, Jun. 1989, pp. 2657-2666.

Schlaeger et al., "SEAP expression in transiently transfected mammalian cells grown in serum-free suspension culture", Cytotechnology 42: pp. 47-55, 2003, Kluwer Academic Publishers, Netherlands.

Massie et al., "New adenovirus vectors for protein production and gene transfer", Cytotechnology 28: pp. 53-64, 1998, Kluwer Academic Publishers, Netherlands.

Berntzen et al., "Prolonged and increased expression of soluble Fc receptors, IgG and a TCR-Ig fusion protein by transiently transfected adherent 293E cells", Journal of Immunological Methods 298, 2005, pp. 93-104, Elsevier B.V.

* cited by examiner

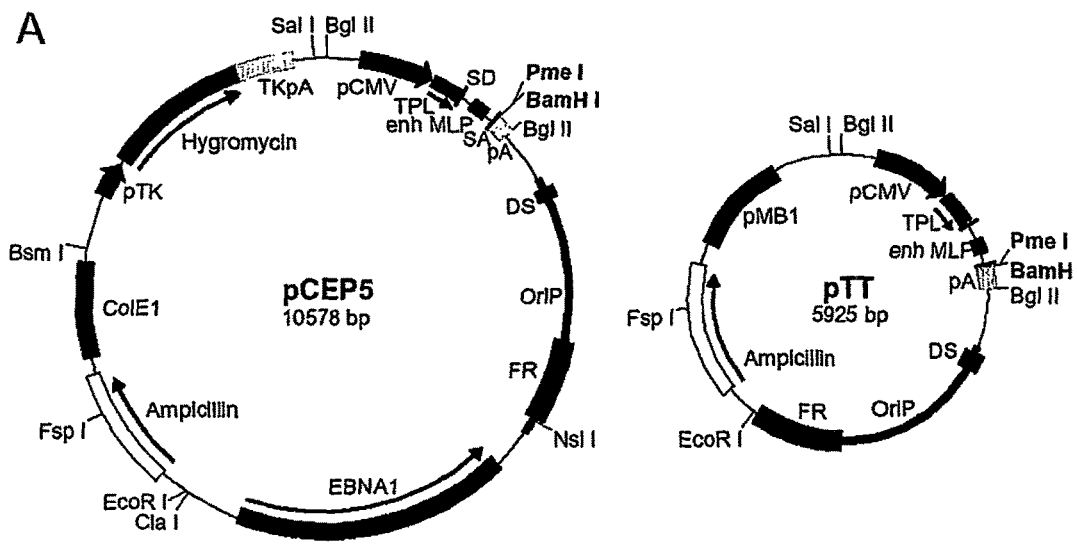
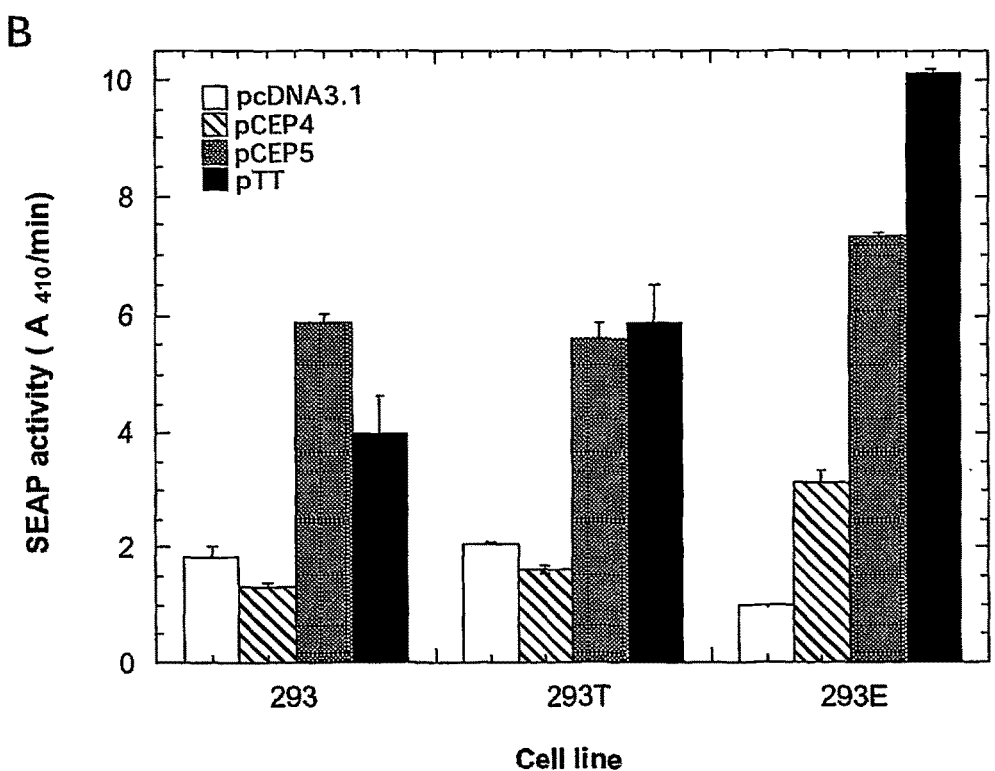
FIG. 2

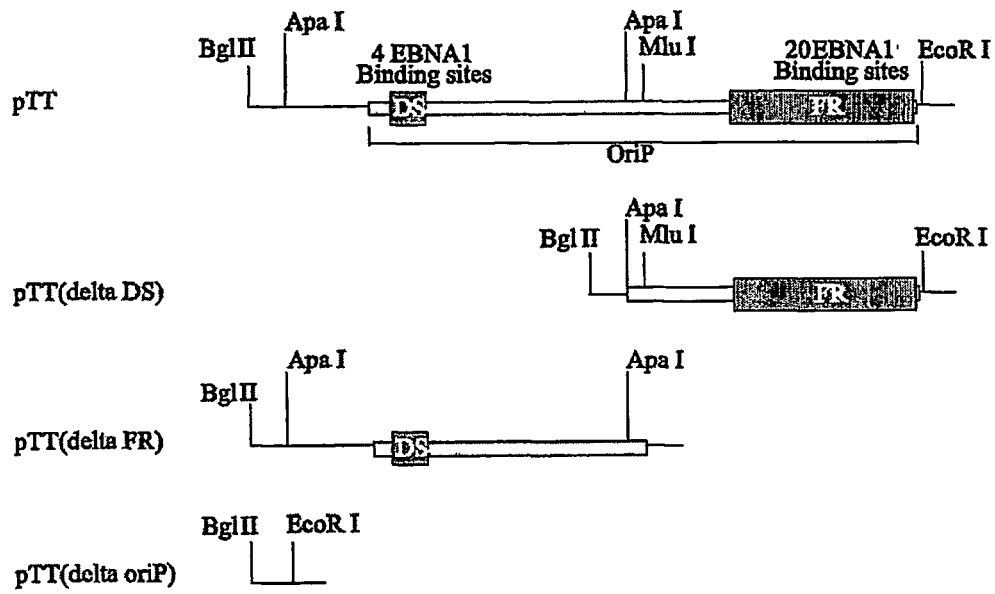
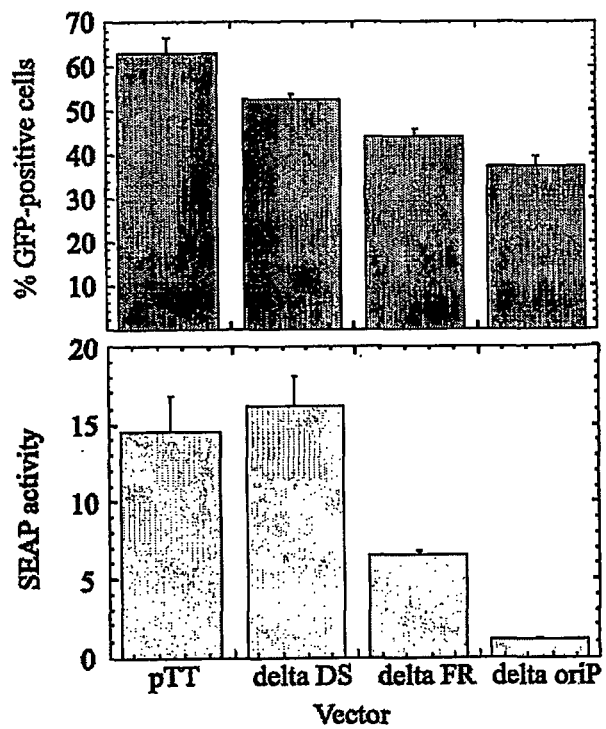
FIG. 6

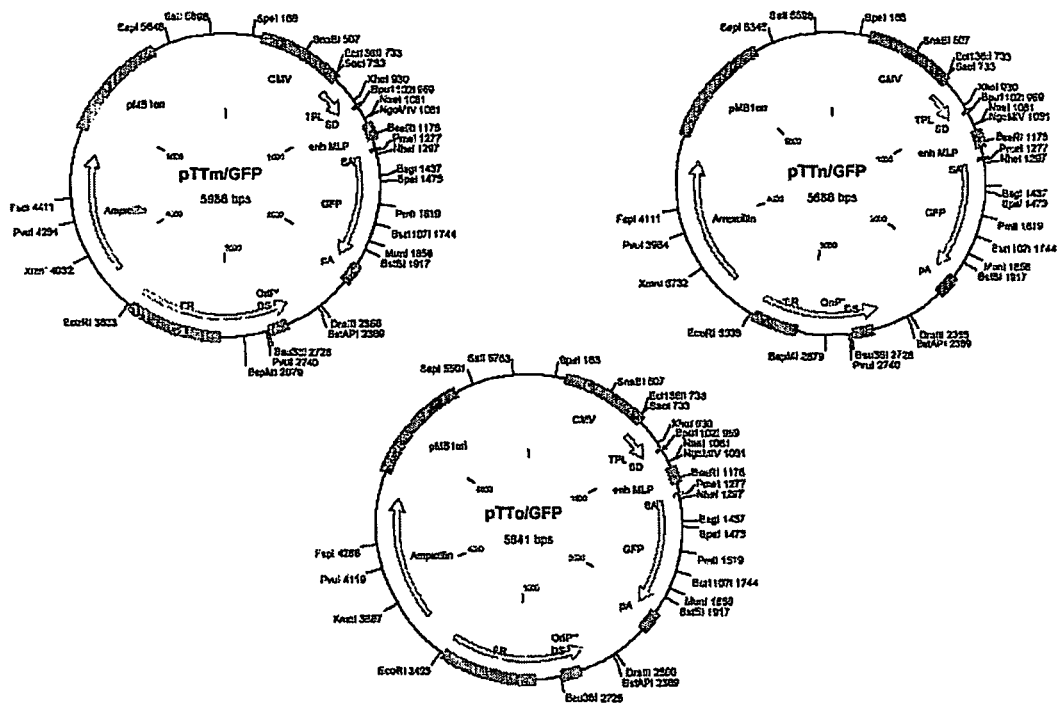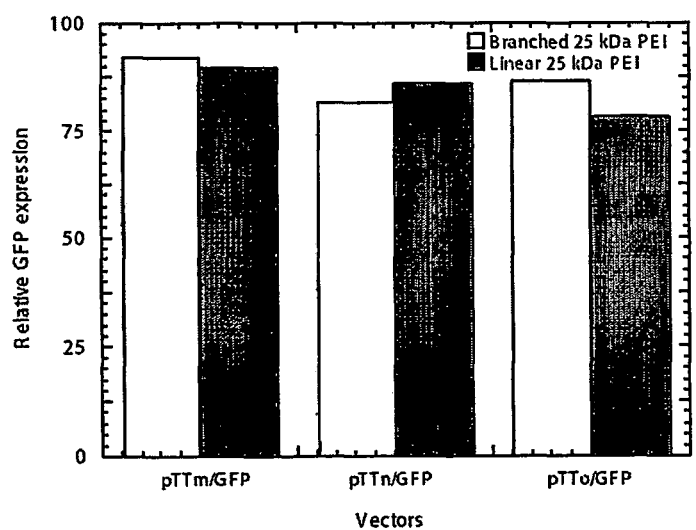
FIG. 7

```
caagaattct catgtttgac agcttatcat cgtgaggata gcatatgcta cccagataca
gattaggata gcatatacta cccagatata gattaggata gcatatgcta cccagatata
gattaggata gcctatgcta cccagatata aattaggata gcatatacta cccagatata
gattaggata gcatatgcta cccagatata gattaggata gcctatgcta cccagatata
gattaggata gcatatgcta cccagatata gattaggata gcatatgcta tccagatatt
       tgggta gtatatgcta cccagatata aattaggata gcatatacta ccctaatctc
tattaggata gcatatgcta cccggataca gattaggata gcatatacta cccagatata
gattaggata gcatatgcta cccagatata gattaggata gcctatgcta cccagatata
aattaggata gcatatacta cccagatata gattaggata gcatatgcta cccagatata
gattaggata gcctatgcta cccagatata gattaggata gcatatgcta tccagatatt
       tgggta gtatatgcta cccatggcaac
```

(SEQ ID NO: 1)

FIG. 8

A
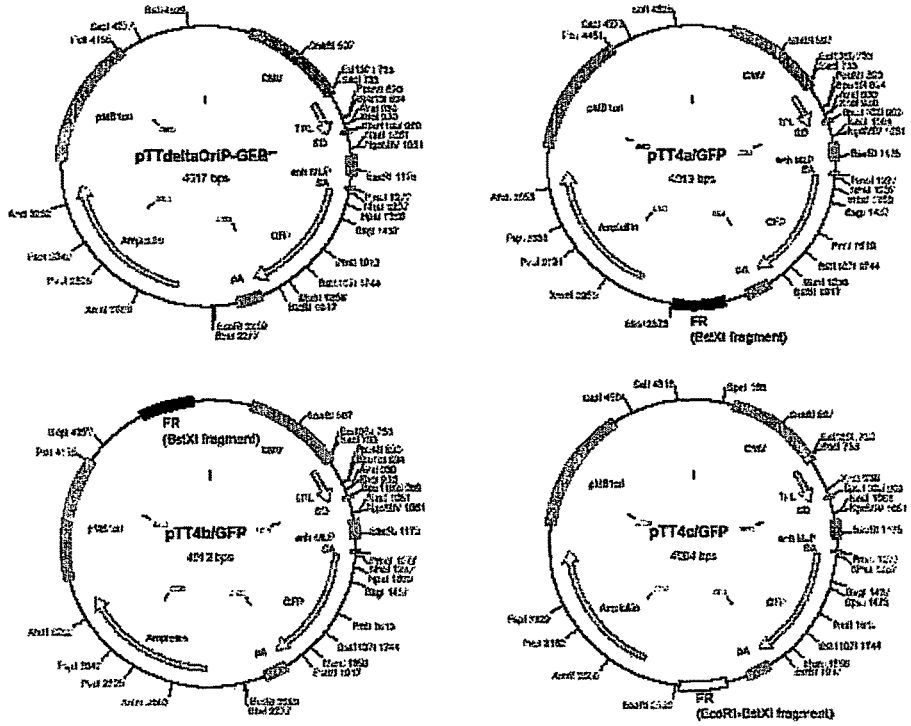
B
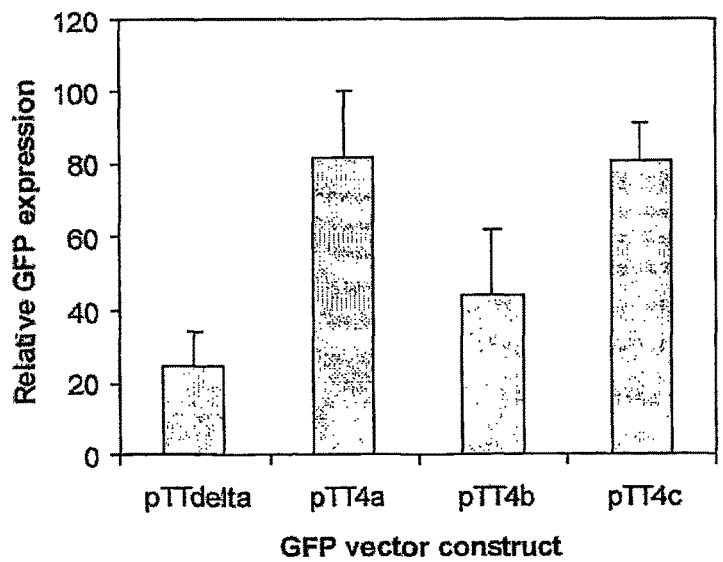
FIG. 9

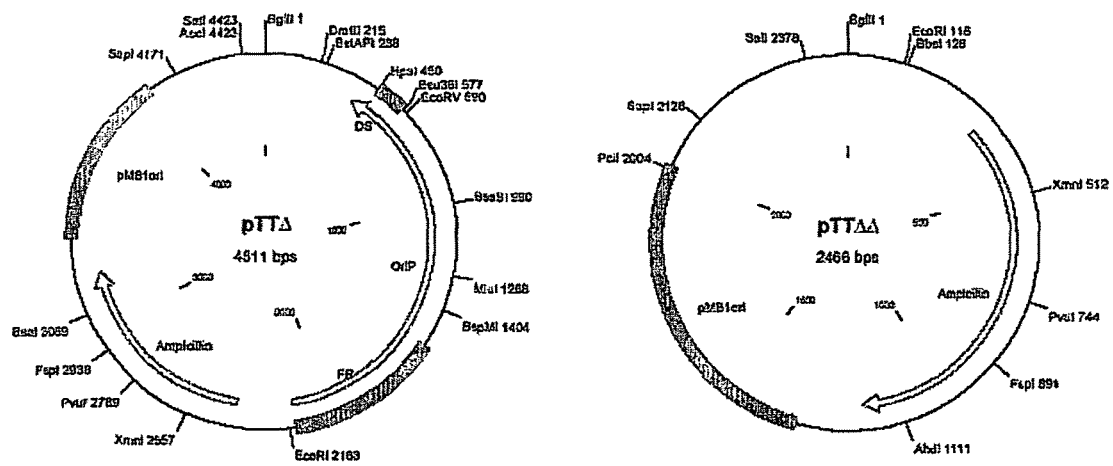
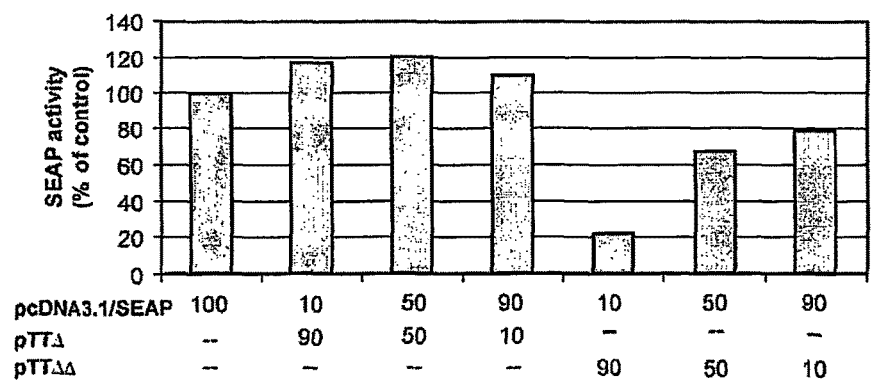
FIG. 10

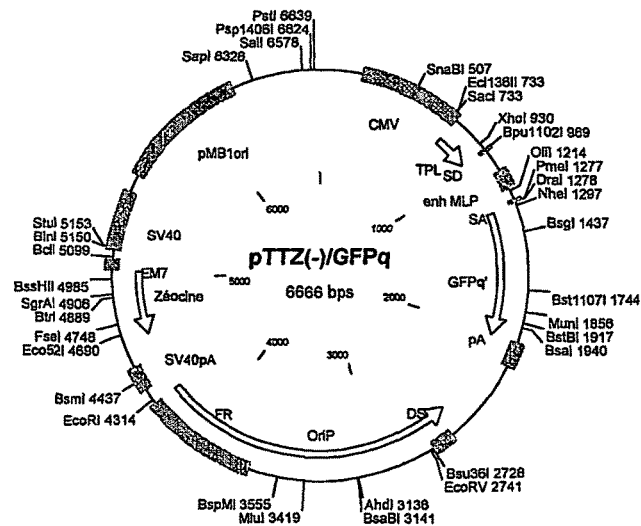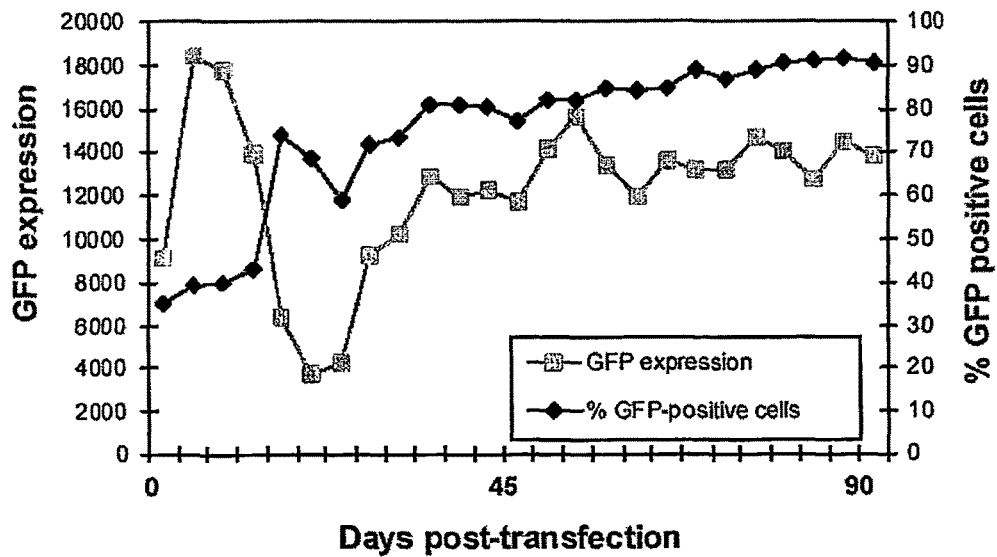
FIG. 15

ENHANCED PRODUCTION OF RECOMBINANT PROTEINS BY TRANSIENT TRANSFECTION OF SUSPENSION-GROWING MAMMALIAN CELLS

This application is a National Phase under 35 U.S.C. 371 of, and claims priority to, International Application No. PCT/CA02/00683,filed May 7, 2002, and claims priority therethrough under 35 U.S,C. § 119 U.S. Provisional Patent Application No. 60/288,790, filed May 7, 2001, the entireties of which are incorporated by reference herein.

FIELD OF THE INVENTION

The invention relates to processes for producing recombinant proteins, in particular to a new process for an enhanced transient expression of a recombinant protein in host mammalian cells, and to new expression vectors, cell lines and culture media adapted to carrying out the process.

BACKGROUND OF THE INVENTION

Mammalian cells are an established expression system in the biotechnology industry for the production of recombinant proteins (r-proteins). In contrast to lower eukaryotes or prokaryotes, mammalian cells provide active r-proteins that possess relevant post-translational modifications. However, in order to obtain sufficient amount of protein for structure/activity analyses or high-throughput screenings, one needs to go through the long and tedious process of stable transfectoma isolation and characterization. As an alternative, the small-scale transient transfection of mammalian cells grown in monolayers can generate significant amount of r-proteins (Cullen B. R., *Methods Enzymol.*, 152, 684-704 (1987); Blasey H. D. et al., *Cytotechnology*, 18, 183-192 (1996); Cachianes G. et al., *Biotechniques*, 15, 255-259 (1993)), but scalability of this process is limited by culture surface availability. The use of the well-established calcium phosphate precipitation technique or the recently described cationic polymer polyethylenimine (PEI) (Boussif O. et al., *Proc, Natl. Acad. Sci. USA*, 92, 7297-7301 (1995)) provides cost-effective ways of introducing plasmid DNA into mammalian cells. A major breakthrough has recently emerged for the fast production of milligram amounts of recombinant proteins when these gene transfer vehicles were shown to be effective for large-scale transient transfection of mammalian cells grown in suspension culture (Jordan M. et al., *Cytotechnology*, 26, 39-47 (1998); Schlaeger E-J. et al, *Cytotechnology*, 30, 71-83 (1999); Wurm F. et al., *Curr. Opin. Biotechnol.*, 10, 156-159 (1999)).

For an optimal large-scale transient transfection and r-protein expression in mammalian cells, four key aspects are to be taken into account, namely 1) the cell line, 2) the expression vector, 3) the transfection vehicle and 4) the culture medium. The human 293 cell line (a human embryonic kidney cell line containing the E1 region of human Ad5 adenovirus DNA) is widely used for r-protein production as it offers many advantages, such as high transfection yields with most common gene transfer vehicles, is easily grown in suspension culture, and can be adapted to serum-free media. Moreover, two genetic variants of the 293 cell line, the 293E and 293T cell lines, expressing the Epstein-Barr virus (EBV) Nuclear Antigen 1 (EBNA1) and the SV40 large-T antigen, respectively, allow episomal (extrachromosomal) amplification of plasmids containing the viral EBV (293E) or SV40 (293T) origins of replication. These cell lines are therefore expected to increase r-protein expression levels, by permitting more plasmid copies to persist in the transfected cells throughout the production phase (Van Craenenbroeck H. et al., *Eur. J. Biochem.*, 267, 5665-5678 (2000)).

The second important issue for high level r-protein expression is the use of vectors having promoters that are highly active in the host cell line, such as the human cytomegalovirus (CMV) promoter (Foecking M. K. et al, *Gene*, 45, 101-105 (1985)). This promoter is particularly powerful in 293 cells, where it has been shown to be strongly transactivated by the constitutively expressed adenovirus E1a protein (Gorman C. M. et al., *Virology*, 171, 377-385 (1989)). Moreover, a highly efficient expression cassette using this promoter has been recently described that provides adenovirus-mediated transgene expression levels reaching up to 20% of total cell proteins (TCP) (Massie B. et al., *J. Virol.*, 72, 2289-2296 (1998); Massie B. et al., *Cytotechnology*, 28, 53-64 (1998)).

The third aspect is related to gene transfer reagent efficacy. Even though many highly effective gene transfer reagents are commercially available, only few are cost-effective when considering operations at the multi-liters scale. For large-scale transient transfection applications, these reagents should also be simple to use, effective with suspension growing cells and have minimal cytotoxic effects. PEI satisfies most of these criteria, as it has high gene transfer activity in many cell lines while displaying low cytotoxicity (Boussif O., supra), is cost-effective, and efficiently transfects suspension growing 293 cells (Schlaeger E-J., supra). This polymer is available as both linear and branched isomers with a wide range of molecular weights and polydispersities, which physicochemical parameters are critical for efficient gene transfer activity (Godbey W. T. et al., *J. Control Release*, 60, 149-160 (1999).

The last key aspect for efficient r-protein expression by transient transfection relates to the culture medium. Some gene transfer reagents work only in serum-free media whereas others are less sensitive to the presence of serum. Also, as the presence of cellular by-products in conditioned medium is associated with poor transfection yield, it is often necessary to perform a complete medium change prior to transfection. However, this step does not satisfy the need for a robust large-scale transient transfection process.

Transient protein expression system are known in the prior art, for example the transient expression system disclosed in U.S. Pat. No. 5,024,939. However, these systems generally suffer from the above-discussed and other drawbacks and limitations and are not well suited to large-scale, high-throughput production of r-proteins. The present invention provides a transient expression system and process which is free of many such prior art limitations.

SUMMARY OF THE INVENTION

The invention provides a new process for the production of recombinant proteins, by transfection of suspension-growing eukaryotic cells with an expression vector comprising a first DNA sequence coding for the desired protein, said first DNA sequence being under control of a suitable promoter, and a second DNA sequence enhancing transcriptional activity of the promoter and increasing nuclear import of the expression vector. In a preferred embodiment, the second DNA sequence additionally supports an episomal replication of the vector in the transfected cells. The eukaryotic cells are preferably mammalian cells, more preferably the human embryonic kidney 293 cell line and its genetic variants, more preferably genetic variants stably expressing the EBNA1 protein or a fragment thereof. The expression vector is preferably a plasmid, comprising the first DNA sequence as a part of an expression cassette, the cassette further comprising the promoter, preferably a cytomegalovirus (CMV) promoter, most preferably the CMV5 promoter. The second DNA sequence is preferably of a viral origin, more preferably the oriP sequence of Epstein-Barr virus (EBV) or a fragment thereof. The transfection is preferably carried out using polyethylenimine (PEI) as a transfection reagent, for example, linear or branched PEI, preferably having an average molecular weight of from 10 to 100 kDa, more preferably using the 25 kDa linear isoform of PEI. The process combines in a single step the cell growth, transfection and protein expression, is carried out using suspension-growing cells without changing the culture medium, and allows to achieve high expression levels in a short period of time. The process may be carried out in a serum-free culture medium, is easily scalable, compatible with continuous production processes, and fully adapted to high-throughput production of milligram quantities of recombinant proteins.

Thus, according to one aspect, the invention provides a process for the preparation of a recombinant protein, said process comprising the steps of: providing eukaryotic host cells suspension-growing in a culture medium; transfecting the host cells in the presence of a transfection reagent with an expression vector, said vector comprising a first DNA sequence encoding the recombinant protein, said first DNA sequence being under control of a promoter; culturing the transfected cells under conditions favoring expression of the recombinant protein, and harvesting the expressed protein.

According to another aspect, the invention provides an expression vector for an enhanced expression of a recombinant protein in a mammalian cell, said vector comprising a first DNA sequence encoding the recombinant protein, said first DNA sequence being under control of a promoter, said expression vector further comprising a second DNA sequence enhancing the transcriptional activity of the promoter and increasing the nuclear import of the expression vector.

According to still another aspect, the invention provides a human embryonic kidney cell line derived from the 293SF-3F6 cell line (ATCC Accession No. CRL-12585), said line constitutively expressing the EBNA1 protein or a fragment thereof.

BRIEF DESCRIPTION OF THE DRAWINGS

FIG. 2 is a graph showing effects of cell line and vector on transient SEAP expression. (A) shows genetic maps of pCEP5 (left) and pTT (right) vectors drawn to scale. The pCEP5 vector backbone is identical to pCEP4 vector except for the transgene expression cassette. The pTT vector was obtained following removal of the hygromycin and EBNA1 expression cassettes and replacement of the ColE1 origin for the pMB1 ori, as described in Material and Methods. TPL: tripartite leader; enh MLP: major late promoter enhancer; SD: splice donor; SA: splice acceptor; DS: dyad symmetry; FR: family of repeats. (B) Cells were transfected with 1 µg of DNA and 2 µg of linear PEI and SEAP activity measured 72 hpt. The pGFP plasmid (0.1 µg) was also added in each condition to monitor for transfection efficiency and SEAP activities were normalized accordingly. Empty boxes: pcDNA3.1/SEAP; hatched boxes: pCEP4/SEAP; gray boxes: pCEP5/SEAP; black boxes: pTT/SEAP vector.

FIG. 6 is a graph showing the contribution of FR and DS domains on transient gene expression. The pTT(delta DS) vector was obtained by ApaI digestion and re-circularisation. The pTT(delta FR) was obtained by MluI-EcoRI digestion, fill-in and re-circularisation. The pTT(delta oriP) vector was obtained by ApaI-EcoRI digestion, fill-in and re-circularisation. The cDNAs encoding GFP and SEAP were cloned into these vectors, followed by transfection of 293E cells. SEAP and GFP were measured 3 days post-transfection.

FIG. 7 is a graph showing the effect of various oriP truncations on transient gene expression. The pTTm/GFP vector was obtained by digesting pTT/GFP vector with EcoRV-MluI, followed by fill-in and re-circularisation. In this construct, the oriP still contains the complete FR and DS domains. The pTTn/GFP vector was obtained by digesting pTTm/GFP vector with BstXI, followed by re-circularisation. This construct has an FR fragment containing only 9 EBNA1 binding sites (see FIG. 8). The pTTo/GFP vector was obtained by digesting pTT/GFP vector with BspMI-EcoRV. This construct contains intact FR and DS domains.

Figure 1:
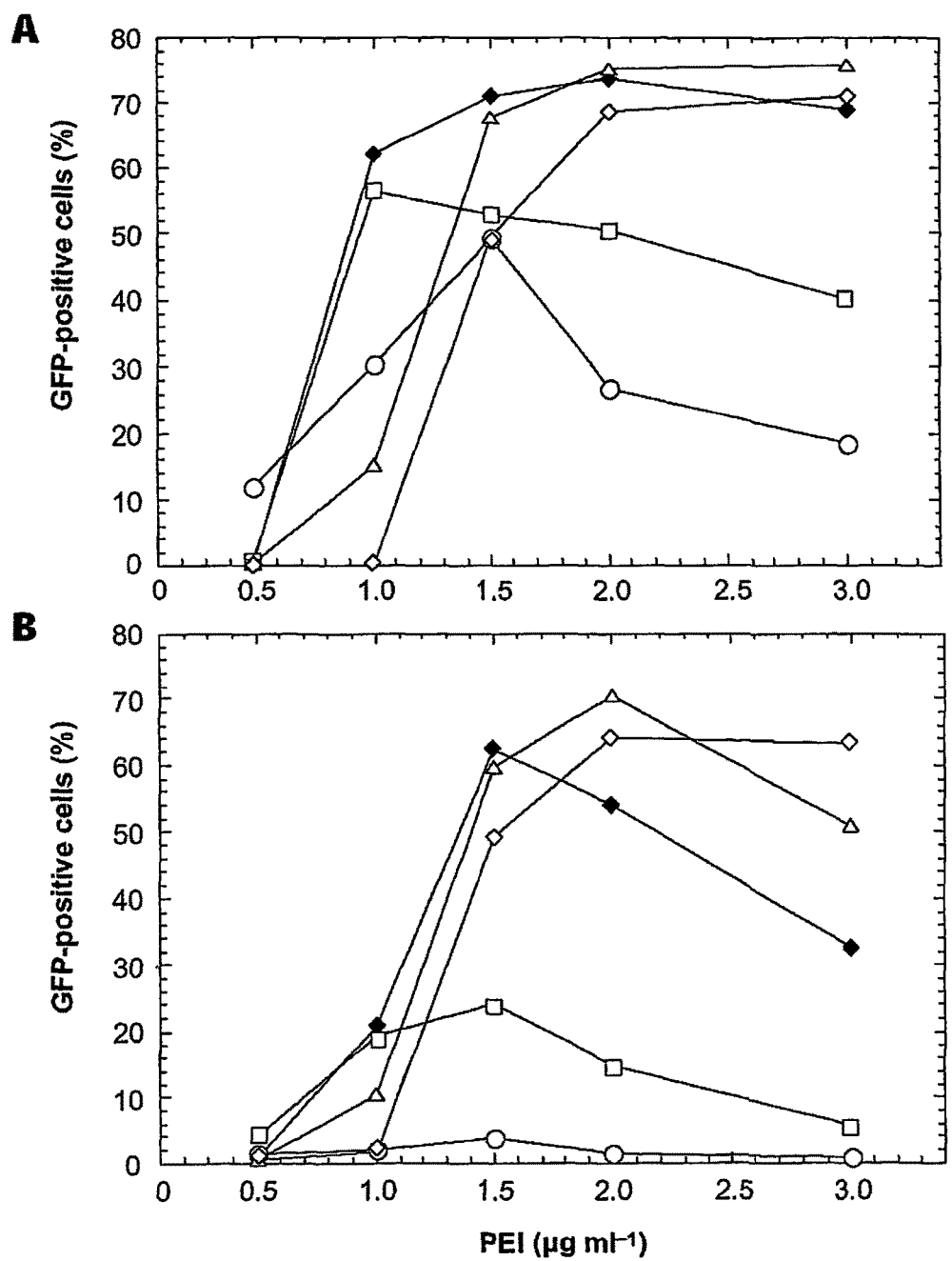
FIG. 1 is a graph showing effects of DNA to PEI ratio on transfection efficiency. 293E cells were transfected with linear (A) or branched (B) 25 kDa PEI at various DNA (pGFP plasmid) concentrations, as described in Material and Methods. DNA concentration ($\mu g\ ml^{-1}$) used were: 0.25 (circles), 0.50 (squares), 1.0 (closed diamonds), 1.5 (triangles), and 2.0 (open diamonds). Transfection efficiencies were determined by flow cytometry analysis 72 hpt.

293E cells were transfected with these constructs and GFP levels measured 3 days later. Results are expressed relative to pTT/GFP vector.

FIG. 8 shows the sequence of the oriP's Family of Repeats (FR). The FR contains 20 EBNA1 binding sites (EBS) (boxed). Spacers between EBS are shadowed. Doubly underlined regions indicate BstXI restriction sites. Nucleotide in bold font indicate mutations in the EBS. Shadowed box indicates EcoRI site.

FIG. 9 is a graph showing the effect of the presence of various FR fragments on transient gene expression. The FR vector constructs used are shown in panel A. The pTT(delta oriP)/GFP vector was derived from pTT/GFP vector following EcoRI-ApaI digestion, T4 DNA polymerase treatment and re-circularisation. The pTT4a/GFP vector contains the BstXI FR fragment (containing 10 EBS) cloned in the EcoRI site of pTT(delta oriP)/GFP vector. The pTT4b/GFP vector contains the BstXI FR fragment cloned in the SalI site of pTT(delta oriP)/GFP vector. The pTT4c/GFP vector contains an FR fragment containing 9 EBS and was derived from pTT(delta oriP)/GFP vector by BstXI-ApaI digestion, T4 DNA polymerase treatment and re-circularisation. 293E cells were transfected with vectors shown in panel A and with pTT/GFP vector. GFP was analyzed by flow cytometry 72 hours later and values expressed relative to the value obtained with pTT/GFP vector (containing the complete oriP) are shown in panel B.

FIG. 10 is a graph showing the effect of oriP on nuclear import of plasmids and gene expression. 293E cells were transfected with pcDNA3.1 plasmid encoding SEAP with or without various ratio of pTTΔ vector (containing the oriP) or pTT-ΔΔ vector (no oriP). SEAP activity was measured 72 hours later.

Figure 11:
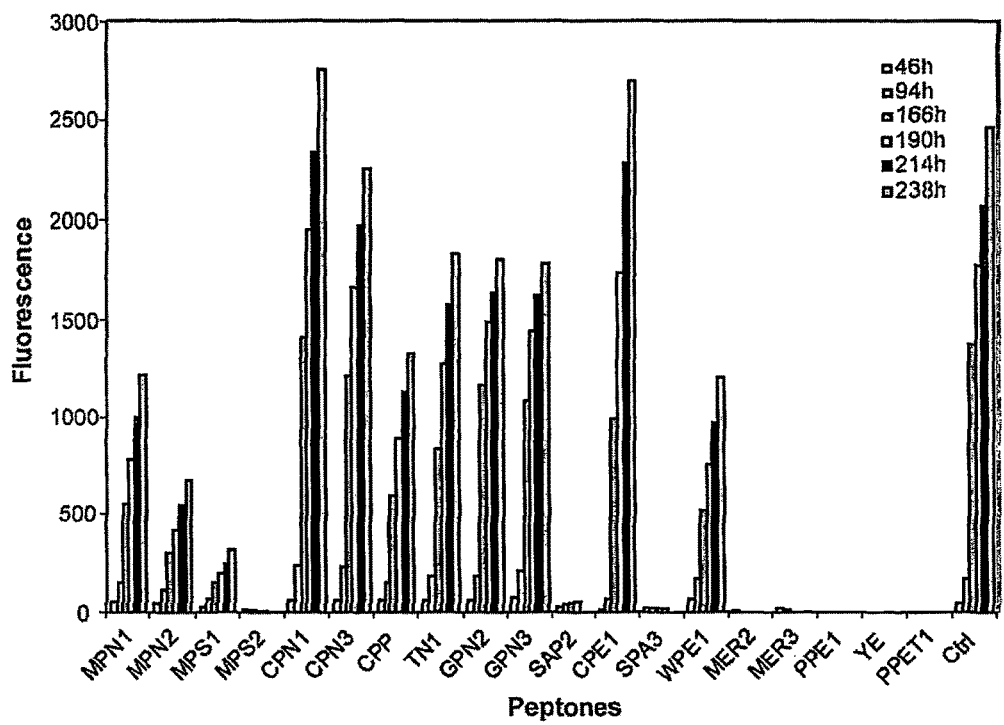

FIG. 11 is a graph showing the effect of peptones on 293E-GFP cells growth. Peptones were tested at 1% (w/v) in HSFM/1% serum. Cells (293E cells stably expressing GFP) were seeded at 1000 cells/well in 96-well plates and fluorescence was monitored daily using a fluorescence microplate reader. Increases in fluorescence indicate cell growth. Control is without peptones. MP: meat peptones; CP: casein peptones; TN: tryptone; GP: gelatin peptones; SP: soy peptones; WP: wheat peptones; ME: malt peptones; PP: plant peptones; YE: yeast extract.

Figure 12:
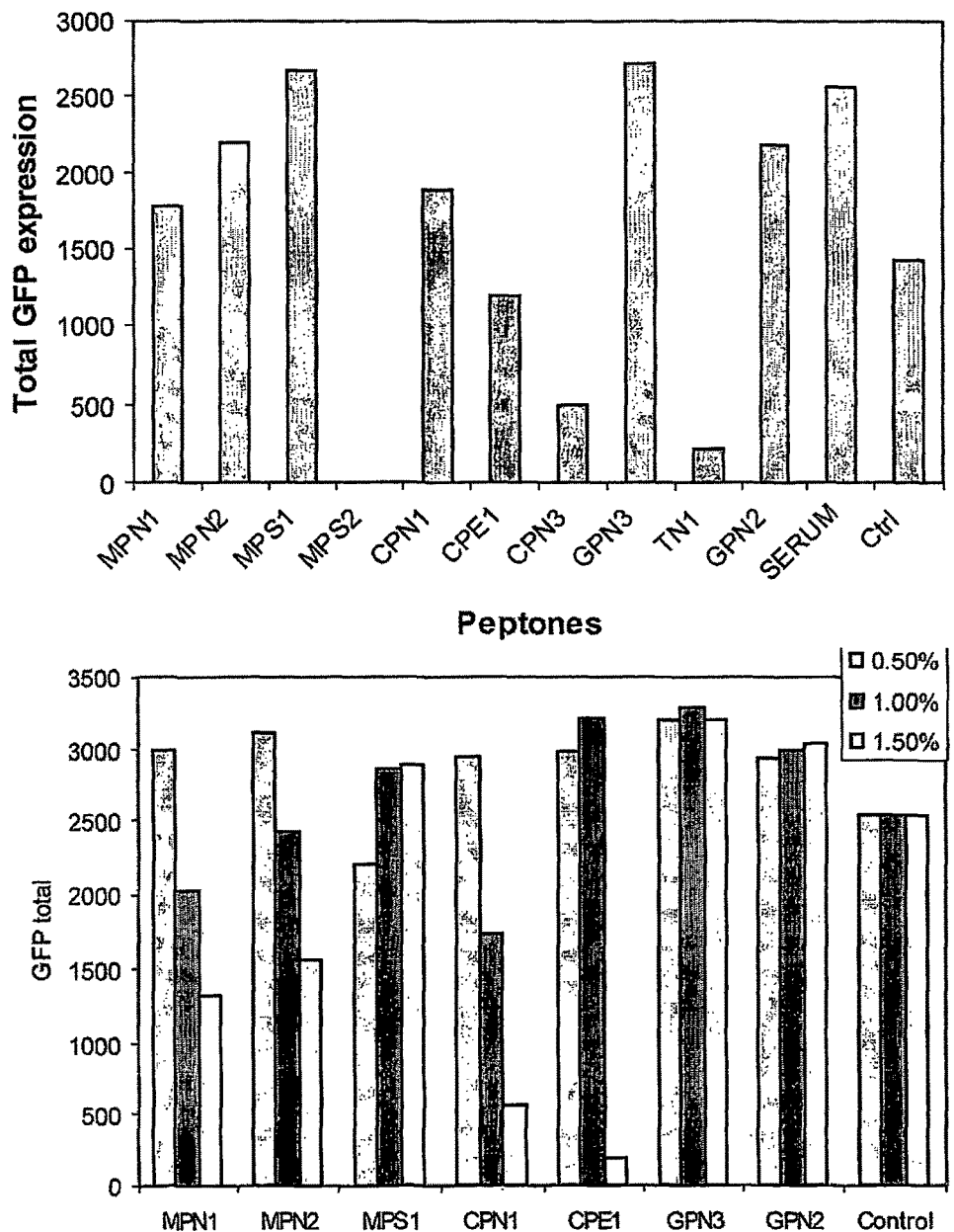

FIG. 12 is a graph showing the effect of peptones and their concentration on transient transfection of SFE cells. Peptones were first tested at 1% (w/v) in HSFM. The effect of concentration of selected peptones was then tested at concentrations 0.5%, 1.0% and 1.5%. GFP was monitored 72 hours later by flow cytometry. Cell agglomeration was significant when using meat and casein peptones (data not shown). Control is without peptone or serum addition.

Figure 13:
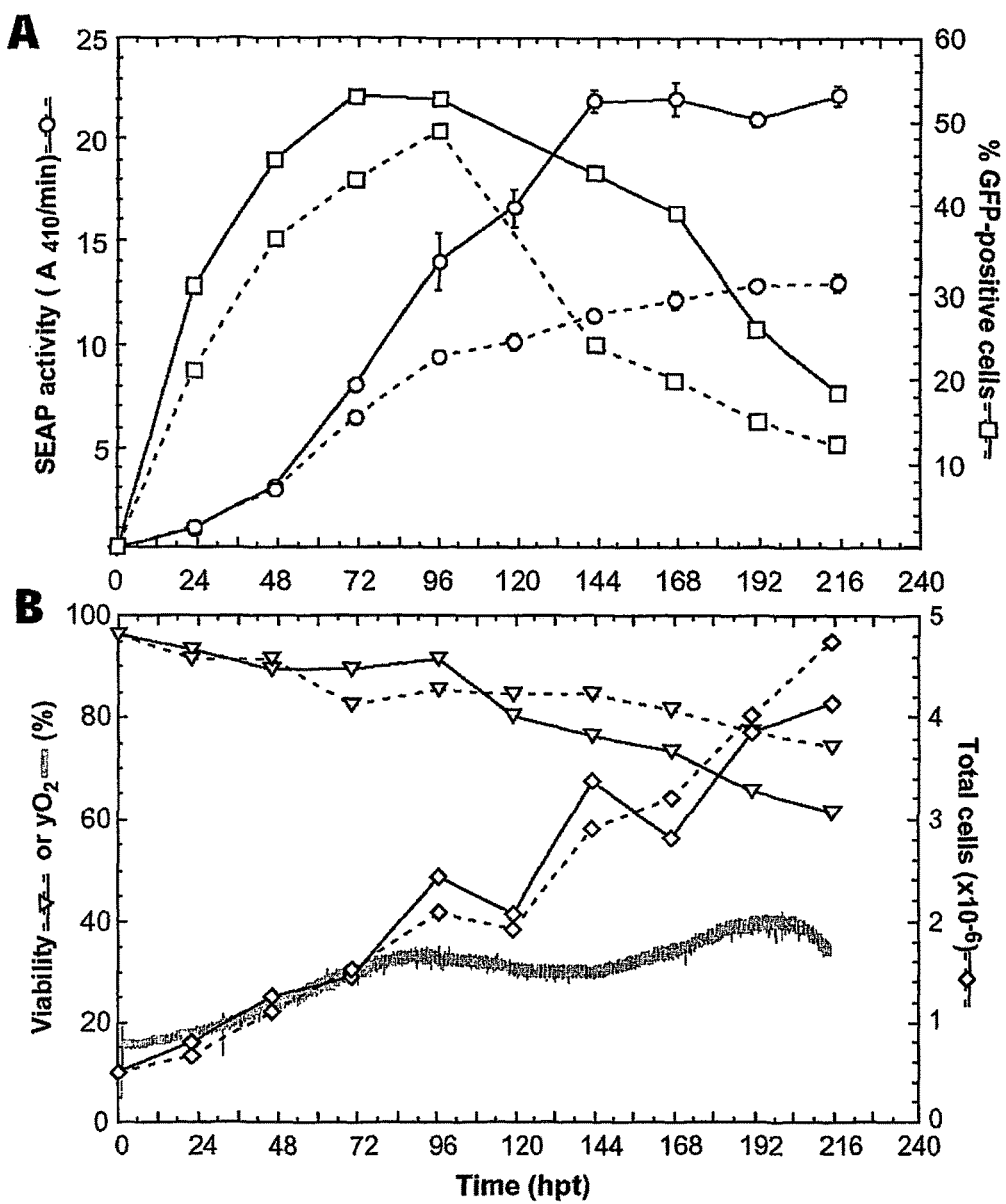

FIG. 13 is a graph illustrating a transient transfection in a 3.5-liters bioreactor. (A) 293E cells were seeded at a density of $2.5 \times 10^5$ ml$^{-1}$ in 2.85 l of fresh HSFM supplemented with 1% BCS. Twenty-four hours later, the transfection mixture (6 mg of linear PEI added to 150 ml HSFM containing 2.85 mg pTT/SEAP and 150 μg pEGFP plasmids) was added to the bioreactor (solid lines). One hour later, 25 ml of culture was withdrawn from the bioreactor and transferred in a shake flask as a control (dashed lines). SEAP activity (circles) and GFP-positive cells (squares) were determined as described in Materials and Methods. (B) Growth curves (diamonds), viability (triangles) and yO$_2$ (gray line) in the 3.5-l bioreactor (solid lines) and shaker flask (dashed lines).

Figure 14:
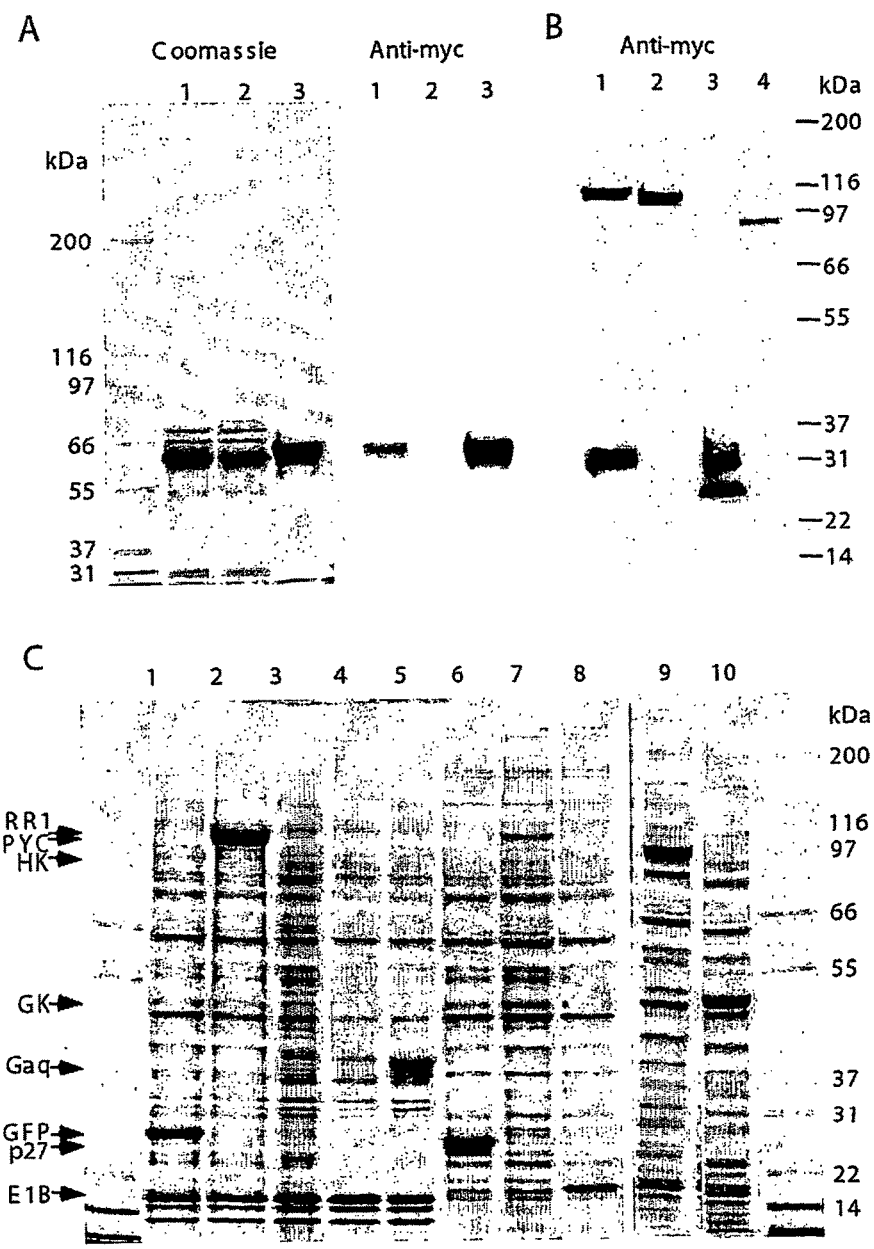

FIG. 14 is a photograph showing results of SEAP purification and production of other secreted and intracellular r-proteins. (A) SEAP purification by IMAC. One liter of culture medium from the 3.5-l bioreactor harvest (FIG. 13) was loaded onto a TALON™ IMAC column (10 ml bed volume). Following extensive washing, bound material was eluted with 150 mM imidazole (20 ml). Ten microliters of culture medium (lane 1), flow-through (lane 2) and eluted material (lane 3) were resolved in duplicate on a 3-8% NuPAGE Tris-acetate gradient gel. One half of the gel was directly stained with Coomassie blue R-250 (left panel) whereas the other half was transferred onto a nitrocellulose membrane and probed with anti-Myc antibody (right panel). (B) Expression of secreted C-terminal Myc-(His)$_6$-tagged r-protein in a 14-l bioreactor. Lane 1, human Neurophilin (1-824; upper band) and VEGF (1-165; lower band) co-transfection in a 1:1 ratio; lane 2, human Tie2 (1-723); lane 3, human Cripto (1-173); lane 4, human c-Met (1-931). Transfections were performed as described in Materials and Methods and culture medium harvested 120 hpt. Fifteen microliters of culture medium were loaded per lane and tagged proteins detected using anti-Myc antibody. (C) Expression of intracellular r-proteins. Lane 1, pTT/sgGFP; lane 2, pTT/RR1; lane 3, pTT empty vector; lane 4, pcDNA3.1/G$_{\alpha q}$; lane 5, pTT/G$_{\alpha q}$; lane 6, pTT/p27$^{KiP1}$; lane 7, pTT/PYC; lane 8, pTT/E1B$^{19K}$; lane 9, pTT/hexokinase; lane 10, pTT/glucokinase. Cells were harvested 72 hpt, rinsed with PBS and solubilized in NuPAGE sample buffer followed by sonication (lanes 1-5) or extracted in lysis buffer (lanes 6-10) as indicated in Materials and Methods. Proteins were resolved on a 4-12% Bis-Tris NuPAGE gradient gel and stained with Coomassie blue R-250.

FIG. 15 is a graph showing the effect of an antibiotic resistance cassette added to a vector. When an antibiotic resistance cassette is added to the vector (in this example the pTTz vector and a zeocin expression cassette) and the antibiotic is added to the cell culture after transfection, a stable population of cells expressing the transgene (in this example GFP) can be obtained is less than a month.

Figure 16:
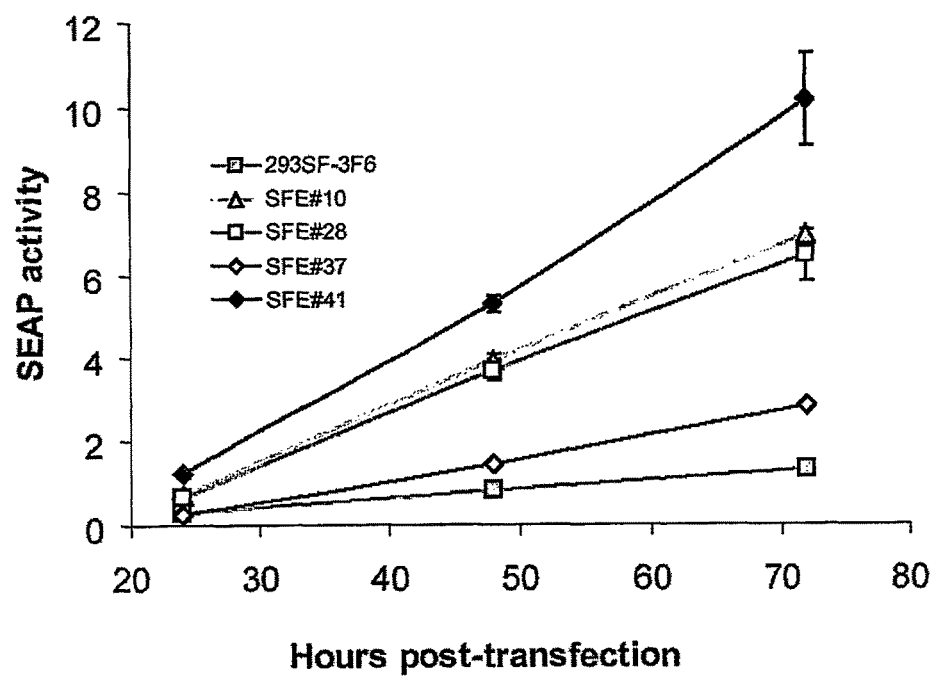

FIG. 16 is a graph showing transient gene expression levels reached in various SFE clones compared to the parental 293SF-3F6 cell line (ATCC Accession No. CRL-12585). Cells were transfected with the pTT/SEAP plasmid. SFE clones were obtained following transfection of the 293SF-3F6 cell line with the pIRES-neo (Clontech) vector encoding the full-length EBNA1 protein and selection using 50 μg/ml of geneticin for two weeks. Resistant cells were seeded at 1 cell/well in 96 well plates and emerging clones amplified and tested for transient gene expression. Of the 20 clones so isolated, only four are shown in the graph, the clone 41 (deposited under IDAC Accession No. 020502) being the one showing the highest transgene expression.

Figure 17:
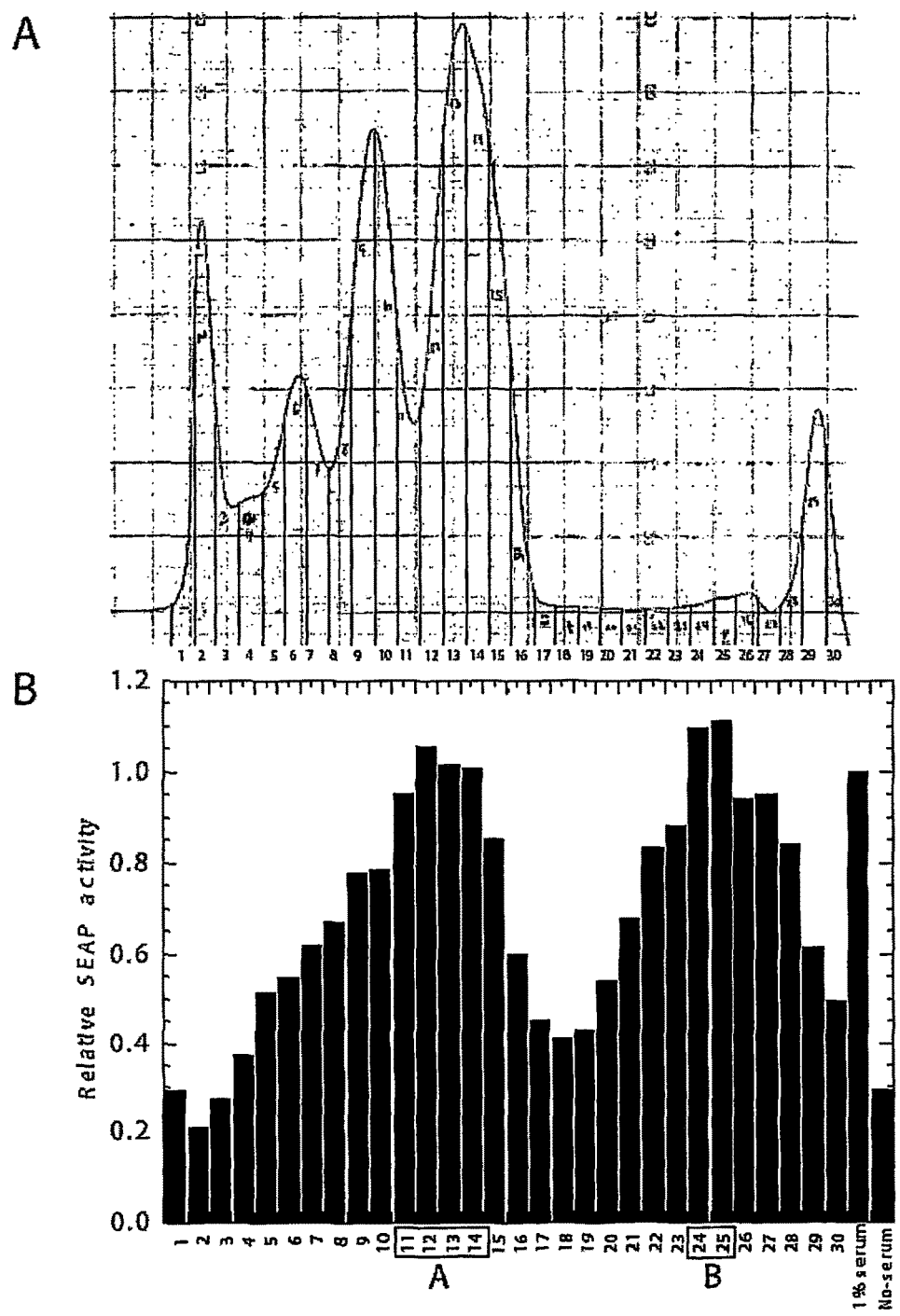

FIG. 17 is a graph showing the effect of the addition of serum sub-fractions on transient gene expression. Panel A shows the bovine calf serum (BCS, Hyclone) protein profile following gel filtration chromatography using a Superdex 200 HR 16/60 column. Fractions were tested at a final concentration of 40% (v/v). Panel B, 293E cells were transfected with the pTT/SEAP vector and SEAP measured 72 hours later. Active fractions were pooled for further analysis (11-14: "fraction A" and 24-25: "fraction B").

Figure 18:
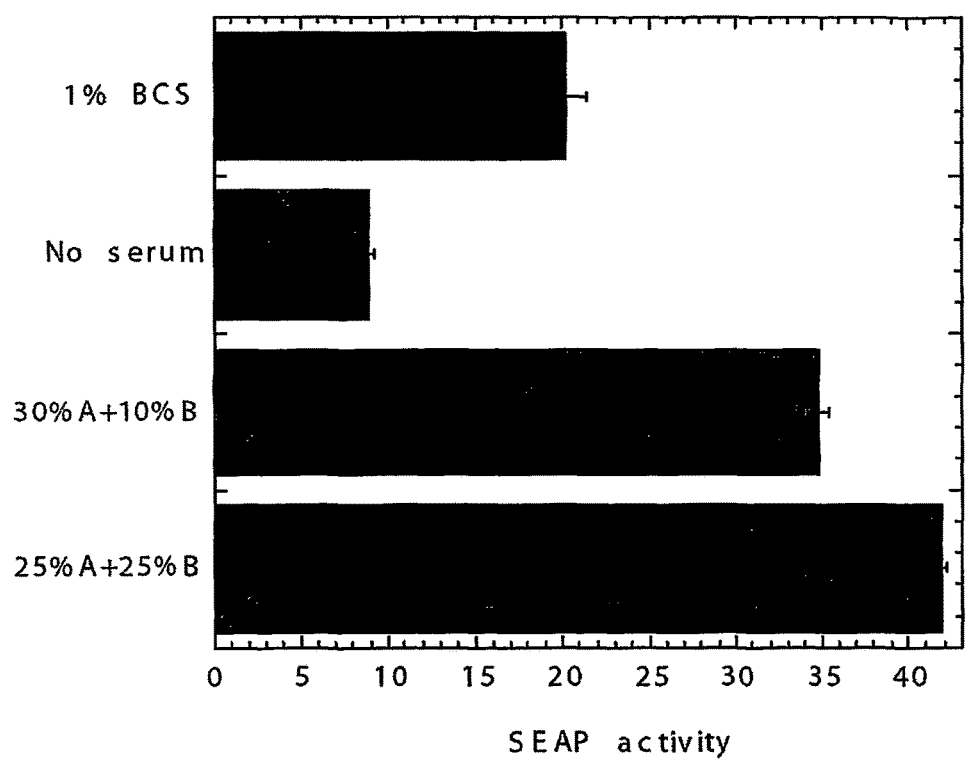

FIG. 18 is a graph showing the effect of the combination of serum "fraction A" and "fraction B" on transient gene expression. 293E cells were transfected with pTT/SEAP in the absence or presence of various ratio of "fraction A" and "fraction B" (see FIG. 17B). SEAP activity was measured 96 hours later. Positive control was medium with 1% BCS and negative control was plain medium.

DETAILED DESCRIPTION OF THE PREFERRED EMBODIMENTS

The present invention provides a new process for an enhanced transient expression of recombinant proteins (r-proteins) in eukaryotic cells, preferably in mammalian cells, most preferably in suspension-growing 293 cell lines.

The process was developed and optimized by investigating the effects of various parameters of the process on r-protein expression, by transient transfection of suspension-growing cells using the polycationic polymer polyethylenimine (PEI) as transfection reagent. In a preferred embodiment, by combining the optimized oriP-containing pTT expression plasmid with the 293E cell line, expression levels of intracellular r-protein representing up to 20% of total cellular proteins (TCP) have been achieved. To the inventors' knowledge, such high expression levels have never been achieved in 293 cells using transient transfection and these levels rival those obtained using virus-mediated transgene expression (Massie B. et al., *Cytotechnology,* 28, 53-64 (1998)). Expression of the human placental secreted alkaline phosphatase (SEAP) protein, one of several proteins expressed using the process of the present invention was found to be at levels exceeding 20 mg/l.

It would be obvious to persons skilled in the art that many different eukaryotic cell lines, in particular mammalian and human cell lines, could be transfected using PEI as transfecting agent and that such cell lines could be used for the process of the invention. However, the efficacy of transfection, and protein expression levels as a result, vary considerably for various cell lines (see, for example Boussif et al., *Gene Therapy,* 3, 1074-1080 (1996)) and is one of the highest for human embryonic kidney (HEK) 293 cell line. Also the activity of the CMV promoter appears to be one of the highest for HEK 293 cell line, as compared with other mammalian cell lines, which considerably improves expression levels of the recombinant protein when this promoter is used in combination with a human embryonic kidney (HEK) cell line. An additional improvement may be achieved by using the HEK 293E cell line (a genetic variant of 293 cell line, constitutively expressing the Epstein-Barr virus (EBV) EBNA1 protein), in combination with an expression vector comprising the EBV oriP-sequence or a fragment thereof containing EBNA1 binding sites (see FIG. 2B).

Particularly advantageous for carrying out the process of the invention proved to be the SFE cell line, a derivative of the cell line HEK293SF-3F6 (ATCC Accession No. CRL-12585) stably expressing the EBNA1 protein. The SFE cell line was developed by transfecting the 293SF-3F6 cell line with the pIRES-neo vector encoding the full-length EBNA1 protein and isolating and amplifying geneticin-resistant clones so obtained, following procedures well known to those skilled in the art. The isolated clones were then tested for transient expression of the SEAP gene. A clone (clone 41) showing the highest expression levels (see FIG. 16) was deposited under IDAC Accession No. 020502. The SFE cell line offers the advantage over the commercially available HEK 293E cell line of being capable of growing in a serum-free medium. Production of secreted r-proteins in a serum-free medium considerably facilitates their subsequent purification. The SFE cell line, known as the HEK293SFE cell line, was deposited at the International Depositary Authority of Canada (IDAC), 1015 Arlington Street, Winnipeg, Canada R3E 3R2 (Telephone (204) 789-2070; Facsimile (204) 789-2097) under IDAC Accession Number 020502 on May 2, 2002 for patent purposes under the terms of the Budapest Treaty. The deposited cell line is a derivative of 293SF-3F6 which is a subclone of the Human Embryonic Kidney cell line 293S, which in turn is derived from HEK293 cells. Access to said biological deposit under the above designation during the pendancy of the instant application shall be available to one determined by the Commissioner of Patents and Trade-marks to be entitled thereto under 37 CRF 1.14 and 35 USC 122 and all restrictions or availability to the public of said biological deposit will be irrevocably removed upon grant of a US patent on the instant application. The deposit will be maintained with all the care necessary to keep it viable and uncontaminated for a period of at least five years after the most recent request for the furnishing of a sample of the deposit and, in any case, for a period of at least thirty (30) years after the date of deposit on the enforceable life of the patent, whichever period is longer.

The use of amplifiable expression cassettes in mammalian cells, such as the dihydrofolate reductase or glutamine synthetase systems, have been shown to result in the isolation of stable call lines showing very high levels of r-protein expression. As an alternative to these stable amplified systems, vectors with viral-derived elements that allow for episomal replication and amplification, such as the large-T antigen/SV40 ori, or the EBNA1/oriP, are well suited when using transient expression systems (Van Craenenbroeck K. et al., *Eur. J. Biochem.,* 267, 5665-5678 (2000)). Although plasmid DNA containing the SV40 ori was shown to replicate in the large-T antigen expressing 293T cell line (Heinzel S. S. et al., *J. Virol.,* 62, 3738-3746 (1988)), it was now shown that it did not provide higher transgene expression in 293T cells when compared with the 293 parental cell line. In contrast, the use of oriP-containing plasmids in 293E cells significantly increased transgene expression compared with the non-permissive 293 cells. This suggests that the increased transgene expression obtained using EBV replicon-containing plasmids might be mediated by a phenomenon distinct from its ability to support episomal replication. This is further supported by the fact that removal of DS domain of oriP, which is responsible for initiation of DNA replication in EBNA1 positive cells (Wysokensky D. A. et al., *J. Virol.,* 63, 2657-2666 (1989)), did not significantly reduce transgene expression (see FIG. 6). One likely mechanism for this oriP-mediated increased expression could arise from the described EBNA1-dependent enhancer activity of oriP (Reisman D. et al., *Moll. Cell. Biol.,* 6, 3838-3846 (1986); Sugden B. et al., *J. Virol.,* 63, 2644-2649 (1989); Gahn T. A. et al., *J. Virol.,* 69, 2633-2636 (1995)). The EBV oriP contains 24 EBNA1 binding sites (Mackey D. et al., *Methods Enzymol.,* 306, 308-328 (1999)). As EBNA1 has an efficient nuclear localization signal (Ambinder R. F. et al., *J. Virol.,* 65, 1466-1478 (1991); Längle-Rouault F. et al., *J. Virol.,* 72, 6181-6185 (1998)), its binding to plasmids bearing oriP may also increase their nuclear import, thus enhancing transgene expression. This effect is illustrated in FIG. 10, where co-transfection of the pcDNA3.1/SEAP plasmid (no oriP) with an oriP empty vector in a ratio of only 1:9 maintained specific SEAP production. In contrast, a co-transfection using the same ratio with an empty vector without oriP lead to a five-fold decrease in specific SEAP production. This suggests that the presence of an oriP vector in PEI-DNA complexes is sufficient to increase nuclear import of non-oriP vectors that are present in the same complexes, thus increasing protein expression. Indeed, the most important barrier to transfection seems to be the limited migration of plasmid DNA from the cytoplasm to the nucleus (Zabner J. et al., *J. Biol. Chem.,* 270, 18997-19007 (1995)). Contribution of this mechanism to the enhanced transgene expression could be partially hindered when using PEI as the transfection reagent, as this polymer was also shown to actively undergo nuclear localization (Pollard H. et al., *J. Biol. Chem.*, 273, 7507-7511 (1998); Godbey W. T. et al., *Proc. Natl. Acad. Sci. USA*, 96, 5177-5181 (1999)). However, data presented in FIG. 9 clearly show a significant contribution of oriP to an enhanced nuclear transport of plasmid DNA.

Whereas linear 25 kDa PEI was reported to efficiently mediate gene transfer in the presence of serum (Boussif O. et al., *Gene Ther.*, 3, 1074-1080 (1996)), transgene expression mediated by the branched isoform was shown to be reduced 3-fold in its presence (Schlaeger E-J. et al., *Cytotchnology*, 30, 71-83 (1999)). This contrasts with findings of the present invention showing that gene transfer was also significantly increased using the branched 25 kDa PEI.

Figure 3:
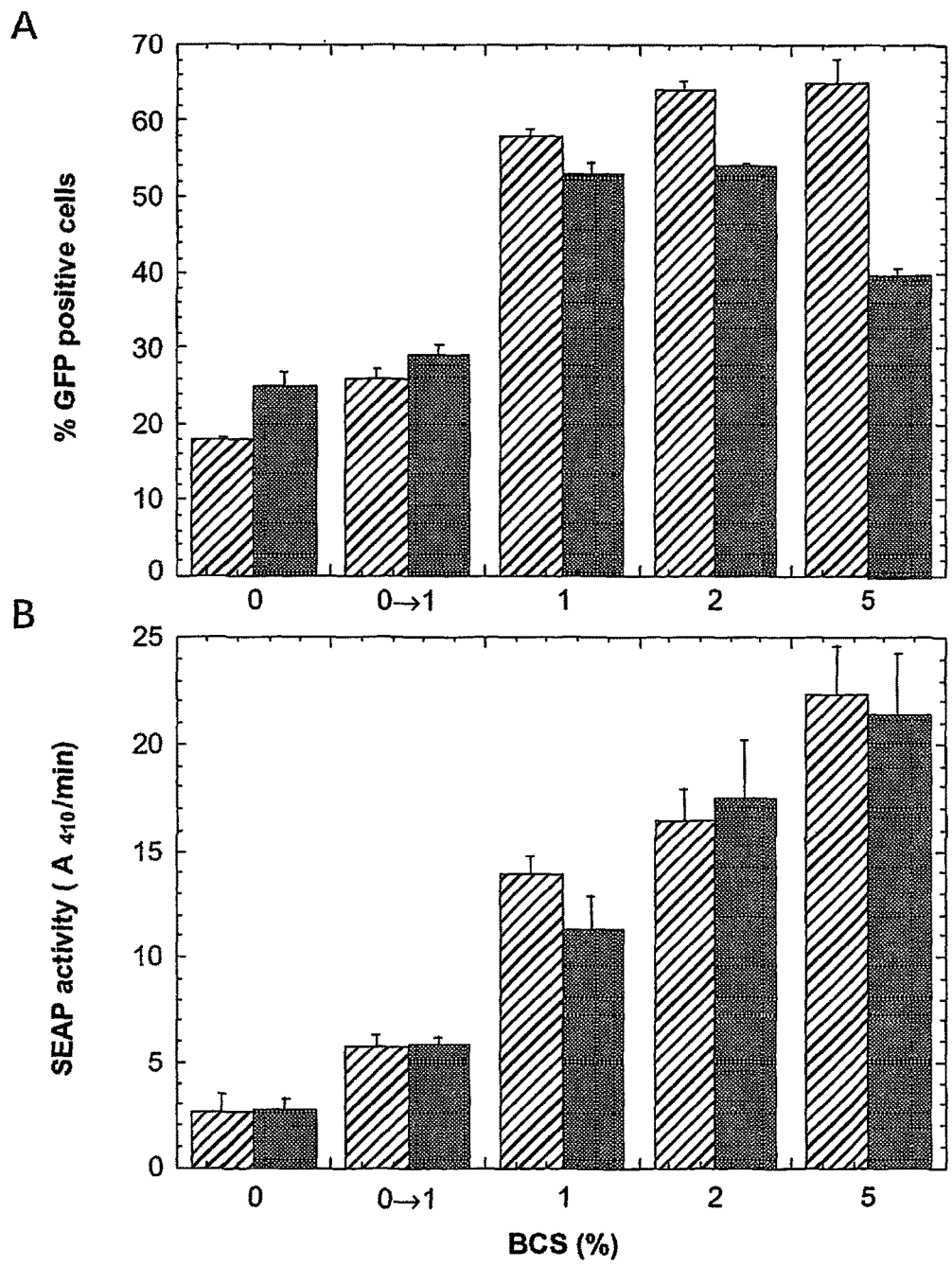
FIG. 3 is a graph showing effects of serum on transgene expression. 293E cells were transfected with pTT/GFPq (A) or pTT/SEAP (B) vectors using 1.0 µg of DNA and 2.0 µg of linear PEI (hatched boxes) or 1.5 µg and 2.0 µg of branched PEI (gray boxes) in fresh serum-free or serum-supplemented media. In one experiment (0→1%), cells were transfected in serum-free media and serum was added 3 hours later to a final concentration of 1%. GFP-positive cells and SEAP activity were measured 72 hpt.

A positive effect of serum as a component of the culture medium on transfection efficiency and protein expression was also observed (see FIG. 3). The mechanism by which serum increases gene delivery and/or transgene expression is not yet clear. Serum might contribute to augment transcriptional activity of the promoter as the CMV immediate early enhancer contains multiple binding sites for serum-activated transcription factors (Boshart M. et al., *Cell*, 41, 521-530 (1985); Brightwell G. et al., *Gene*, 194, 115-123 (1997)). However, only a partial recovery of transgene expression was obtained when serum was added to the cells 3 hrs after their transfection in serum-free medium. This suggests that, in addition to the potential serum-mediated CMV promoter transcription activation, some serum component(s) might increase transfection efficacy of DNA-PEI complexes. The results shown in FIGS. 17 & 18 demonstrate that following serum fractionation, inhibitory components (such as BSA) can be removed, and fractions enhancing transfection and/or transgene expression can be isolated. Further purification of the active components will allow to obtain an additive with minimal protein content (compared to whole serum), that will greatly increase production yields.

As attempts to adapt the commercially available 293E cell line to serum-free medium were unsuccessful, it was decided to create an EBNA1-expressing cell line growing in a serum-free medium by stably transfecting the serum-free adapted 293SF-3F6 clone with an EBNA1 expression plasmid (pIRESneo/EBNA1). Among multiple clones tested, the clone 41 showed the highest transgene expression following transient transfection of the pTT/SEAP plasmid (a ten-fold increase in SEAP expression compared to the 293SF-3F6 parental clone; see FIG. 16). Using this clone, the serum-free medium formulation was further improved in order to reach higher transient gene expression. Of various peptones tested as additives to the serum-free medium, the gelatin peptones GPN3 proved to be the most suitable for this purpose. Other peptones were similarly effective (see FIG. 12), but induced significant cell agglomeration, an undesirable phenomenon in suspension cultures. BSA was removed form the culture medium, as this protein proved to significantly inhibit the transfection and gene expression (data not shown).

A major drawback of using polycations or cationic lipids is the inhibitory effect of conditioned medium on gene delivery. In the case of cationic lipids, this inhibition was shown to be mediated by the presence of secreted glycosaminoglycans (Rupoen M. et al., *Biochim. Biophys. Acta*, 1415, 331-341 (1999); Belting M. et al., *J. Biol. Chem.*, 274, 19375 0 19382 (1999)), which are expected to efficiently displace DNA from lipid complexes. Whereas it was shown that conditional medium adversely reduced PEI-mediated transfection of 293E cells (Schlaeger E-J. et al., supra), no significant effect was observed by the inventors. The reason for this discrepancy is not clear, but might result from the type of culture medium used, the age of the culture, or from the cells themselves. The fact that, according to the invention, transfection of cells in their 24 hr-conditioned medium does not reduce gene transfer and expression, greatly simplifies process scale up.

In conclusion, a significant improvement in transgene expression following transient transfection of suspension-growing cells using PEI was obtained by combining optimized parameters, such as the pTT expression vector, the 293E or 293SFE cell lines, the culture medium, and the transfection process. Under these conditions, ~60 mg of purified SEAP could be obtained from a 3-l culture following a single IMAC purification step. Volumetric expressions of the intracellular proteins GFP and RR1 were, respectively, 20 and 50 mg/l at 72 hpt, representing up to 20% of TCP. As this technology is robust, inexpensive and easy to perform, it is fully adapted for high-throughput production of milligram quantities of r-proteins needed for biochemical or structural studies and high-throughput screenings.

EXPERIMENTAL

Materials and Methods

Chemicals

A 25 kDa branched PEI was obtained from Aldrich (Milwaukee, Wis.) and 25 kDa linear PEI from Polysciences (Warrington Pa.). Stock solutions (1 mg ml$^{-1}$) were prepared in water, neutralized with HCl, sterilized by filtration (0.22 μm), aliquoted and stored at −80° C.

Cell Culture

Human embryonic kidney 293S (293) cells (Côté J. et al., *Biotechnol. Bioeng.*, 59, 567-5765 (1998)) and genetic variants stably expressing EBNA1 (293E) (Invitrogen, Carlsbad, Calif.) or the large-T antigen (293T) (DuBridge R. B. et al., *Mol. Cell. Biol.*, 7, 379-387 (1987)) were adapted to suspension culture in low-calcium-hybridoma serum-free medium (HSFM) (Côté J. et al., supra) supplemented with 1% bovine calf serum (BCS), 50 μg ml$^{-1}$ Geneticin (for 293E and 293T cells), 0.1% Pluronic F-68 (Sigma, Oakville, Ontario, Canada) and 10 mM HEPES. For culture in bioreactors, HEPES was omitted from the medium. Cells were cultured in Erlenmeyer flasks (50 or 125 ml) using 15-25% of the nominal volume at 110-130 r.p.m. (Thermolyne's BigBill orbital shaker, TekniScience Inc., Terrebonne, Québec, Canada) under standard humidified conditions (37° C. and 5% CO$_2$).

Vectors

The pIRESpuro/EGFP (pEGFP) and pSEAP basic vectors were obtained from Clontech (Palo Alto, Calif.), and pcDNA3.1, pcDNA3.1/Myc-(His)$_6$ and pCEP4 vectors were from Invitrogen. The SuperGlo GFP variant (sgGFP) was from Q•Biogene (Carlsbad, Calif.). Construction of pCEP5 vector was as follows: the CMV promoter and polyadenylation signal of pCEP4 were removed by sequential digestion and self-ligation using SalI and XbaI enzymes, resulting in plasmid pCEP4Δ. A BglII fragment from pAd-CMV5 (Massie B. et al., *J. Virol.*, 72, 2289-2296 (1998) 11) encoding the CMV5-poly(A) expression cassette was ligated in BglII-linearized pCEP4Δ, resulting in pCEP5 vector. The pTT vector was generated following deletion of the hygromycin (BsmI and SalI excision followed by fill-in and ligation) and EBNA1 (ClaI and NsiI excision followed by fill-in and ligation) expression cassettes. The ColE1 origin (FspI-SalI fragment, including the 3' end of β-lactamase ORF) was replaced with a FspI-SalI fragment from pcDNA3.1 containing the pMB1 origin (and the same 3' end of β-lactamase ORF). A Myc-(His)$_6$ C-terminal fusion tag was added to SEAP (HindIII-HpaI fragment from pSEAP-basic), following in-frame ligation in pcDNA3.1/Myc-His (Invitrogen) digested with HindIII and EcoRV. To insert a SV40 promoter—zeocin-SV40 polyA expression cassette into the pTT vector (resulting in pTTz vector), the cassette was first amplified from pZeo(SV2+) vector (Invitrogen) using primers with BspHI sites at their extremities. The amplified cassette was then ligated between the BspHI sites of pTT vector. All plasmids were amplified in *Escherichia coli* (DH5α) grown in LB medium and purified using MAXI prep columns (Qiagen, Mississauga, Ontario, Canada). For quantification, plasmids were diluted in 50 mM Tris-HCl pH 7.4 and the absorbances at 260 and 280 nm measured. Only plasmid preparations with $A_{260}/A_{280}$ ratios between 1.75 and 2.00 were used.

Small-Scale Transient Transfections

Three hours before transfection, cells were centrifuged and resuspended in fresh HSFM medium supplemented with 1% BCS at a density of $1.0 \times 10^6$ cells ml$^{-1}$. Five hundred microliters, or 10 ml, of cell suspension was distributed per well of a 12 well plate, or in a 125 ml shaker flask, respectively. DNA was diluted in fresh serum-free HSFM (in a volume equivalent to one-tenth of the culture to be transfected), PEI was added, and the mixture immediately vortexed and incubated for 10 min at room temperature prior to its addition to the cells. Following a 3 h incubation with DNA-PEI complexes, culture medium was completed to 1 ml (12-well plate) or 20 ml (shaker flask) by the addition of HSFM supplemented with 1% BCS.

Transfection in Bioreactors

A 3.5-l bioreactor containing 2.85 l of HSFM supplemented with 1% BCS was seeded with 293E cells to obtain a final cell density of $2.5 \times 10^5$ ml$^{-1}$. Twenty-four hours later, cells were transfected with 150 ml of a mixture of pTT/SEAP:pEGFP plasmids (19:1, 3 mg total) and PEI (6 mg). Agitation was at 70 r.p.m. using a helical ribbon impeller (Kamen A. A. et al., *Chem. Eng. Sci.*, 27, 2375-2380 (1992)). Dissolved oxygen was maintained at 40% by surface aeration using a nitrogen/oxygen mixture (300 ml/min) and pH was maintained at 7.2 by addition of $CO_2$ in the head space and sodium bicarbonate (10% w/v in water) injection in the culture medium. The same conditions were used for transfection in 14-l bioreactors.

Flow Cytometry

GFP was analyzed by flow cytometry using an EPICS Profile II (Coulter, Hialeah, Fla., USA) equipped with a 15-mW argon-ion laser. Only viable cells were analyzed for the expression of GFP. Data are representative of at least two independent experiments. Error bars represent ±SEM of one experiment done in duplicate SEAP Analysis Determination of SEAP activity was performed essentially as previously described (Durocher et al., *Anal. Biochem.*, 284, 316-326 (2000)). Briefly, culture medium was diluted in water as required (typically 1/50 to 1/1000) and 50 μl were transferred to a 96-well plate. Fifty microliters of SEAP assay solution containing 20 mM paranitrophenyl-phosphate (pNPP), 1 mM $MgCl_2$, 10 mM I-homoarginine and 1 M diethanolamine pH 9.8 were then added and absorbance read at 410 nm at 1-2 min intervals at room temperature to determine pNPP hydrolysis rates. Data are representative of at least two independent experiments. Error bar represent ±SEM of one experiment done in duplicate. For the bioreactor run, error bars represent ±SEM of two SEAP measurements.

Electrophoresis, Western Analyses and Quantification

Immunodetection of C-terminal Myc-(His)$_6$-tagged SEAP was done using the anti-Myc 9E10 antibody (Santa Cruz). For analysis of intracellular proteins, cells were directly lysed in NuPAGE sample buffer (Novex) or extracted with lysis buffer (50 mM HEPES pH 7.4, 150 mM NaCl, 1% Thesit and 0.5% sodium deoxycholate). Insoluble material was removed from lysates by centrifuagtion at 12 000 g at 4° C. for 5 min. Concentrated NuPAGE buffer (4×) was added to clear lysates. All samples were heated for 3 min at 95° C. Proteins were resolved on 4-12% Bis-Tris or 3-8% Tris-acetate NuPAGE gradient gels as recommended by the manufacturer. GFP and other non-tagged proteins were quantified relative to purified bovine serum albumin (BSA) following electrophoresis and Coomassie blue R250 staining using the Kodak Digital Science Image Station 440cf equipped with the Kodak Digital Science 1D image analysis software version 3.0 (Eastman Kodak, NY, USA). RR1 was quantified by slot-blot relatively to a homogeneity-purified RR1 standard detected by using a monoclonal anti-RR1 antibody. Other Myc-(His)$_6$-tagged proteins were quantified relative to purified SEAP-Myc-(His)$_6$.

EXAMPLES

Transfection with Linear and Branched 25 kDa PEI

Preliminary results showed that linear and branched 25 kDa PEI were the most effective among various polymers tested (including branched 70 kDa, branched 50-100 kDa and branched 10 kDa; data not shown). In view of the above, transfection of 293E cells was optimized with both linear or branched 25 kDa PEI polymers using a plasmid encoding the enhanced GFP (pEGFP). Transfections were performed using cells grown as monolayers in 12-well plates and GFP expression was measured 72 hours later by flow cytometry. The effect of DNA to PEI ratios on transfection efficiency is shown in FIG. 1 using linear (A) or branched (B) PEI. The indicated amounts of DNA and polymers are for one well containing $5 \times 10^5$ cells. Only 0.25 μg of DNA per well was sufficient to reach a 50% transfection efficiency when using linear PEI, whereas a minimum of 1.0 μg was necessary using the branched isoform. Transfection efficiencies of ~70% were reached with both linear and branched polymers at DNA:PEI (μg:μg) ratios of 1.0:1.5 and 1.5:2.0, respectively. Increasing the amounts of both DNA and PEI did not lead to higher transfection yield.

Cell Line and Expression Vectors

Two commercially available expression vectors containing viral sequences allowing for episomal DNA replication in permissive cell lines were tested. The first vector, pcDNA3.1, contains the SV40 origin of replication that allows cellular polymerases to replicate the DNA up to 1000-copies in cells expressing the large T antigen (Chittenden T. et al., *J. Virol.*, 65, 5944-5951 (19991)). The second vector, pCEP4, contains the EBV origin of replication oriP that replicates plasmid DNA up to 90-copies in cells expressing the EBNA1 protein (Yates J. L. et al., *Nature*, 313, 812-815 (1985)). Also generated was the pCEP5 vector (FIG. 2A, left) by using an improved CMV expression cassette, as described in the adenoviral transfer vector pAdCMV5 (Massie B. et al., *Biotechnology*, 13, 602-608 (1995)). This expression cassette has been shown to confer very high levels of r-protein expression in 293 cells (Massie B. et al., *Cytotechnology*, 28, 53-64 (1998) 12). The pCEP5 vector was further modified (see Materials and Mathods) to yield the pTT vector (FIG. 2A, right) that is 4.6 kb smaller, hence providing more space for large cDNA cloning. The cDNA encoding for the reporter protein SEAP was then cloned in each of these four vectors and its expression level monitored following transient transfection in 293, 293T or 293E cells. As shown in FIG. 2B, transfection of 293T cell line with the SV40 ori-containing plasmid pcDNA3.1 did not translate into an increased transgene expression when compared with transfection of the parental 293 cells. However, transfection of 293E cells with pCEP4 vector resulted in a 2-3-fold increase in SEAP expression compared with transfection of 293 or 293T cells with the same vector. In addition, the use of pCEP5 vector further increased SEAP expression by a factor of 2-6-fold, depending on the cell line. Finally, the use of the pTT vector in 293E cells resulted in a 33% increase in transgene expression compared with the pCEP5 vector. The overall SEAP expression level in 293E cells was 10-fold higher with the pTT vector compared with pcDNA3.1 vector.

Effect of Serum

The effect of serum on transfection efficiency (GFP) and r-protein production (SEAP) mediated by both linear and branched PEI was evaluated. FIG. 3 shows that when transfection mixture was added to cells in fresh 1% serum-containing medium, a 4-5-fold increase in SEAP activity 72 hpt is obtained compared with its addition to cells in serum-free medium. Increasing serum concentration to 5% further improved PEI-mediated transfection efficiency and production. When transfection mixture was added to cells in serum-free media followed 3 hours later by serum addition to a concentration of 1% (0→1%), a 2-fold increase in transgene expression was obtained; however, this level was only 50% of that obtained in 1% serum.

Process Optimization for Transfection in Suspension

Figure 4:
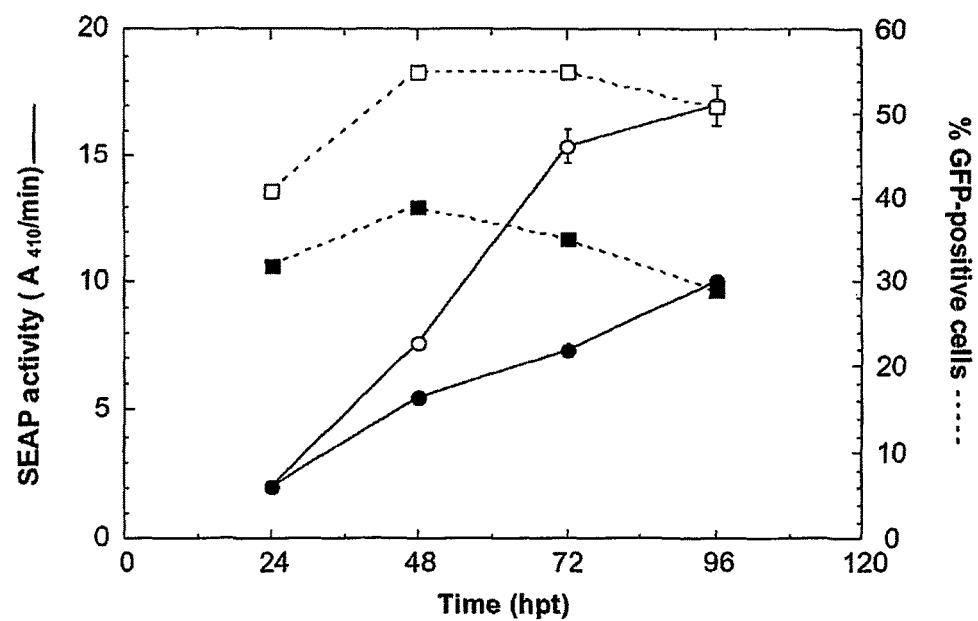
FIG. 4 is a graph illustrating the progress of transfection of suspension growing cells. Cells were resuspended in 10 ml of fresh HSFM containing 1% BCS to a density of $1 \times 10^6$ $ml^{-1}$ in 125 ml Erlenmeyer flask. Three hours later, 1 ml of the DNA-PEI complexes were added and the culture incubated for an additional 3 h. The volume was then completed to 20 ml with fresh culture medium. The DNA-PEI complexes were as follows: 40 µg of linear or branched PEI was added to 1 ml of HEPES-supplemented HSFM containing 18 µg of pTT/SEAP and 2 µg of pEGFP or 27 µg of pTT/SEAP and 3 µg of pEGFP, respectively. Open symbols: linear PEI; closed symbols: branched PEI. Circles: SEAP activity; squares: % GFP-positive cells.

Next evaluated was gene transfer efficiency of both linear and branched PEI on suspension-growing 293E cells grown in 1% BCS-supplemented HSFM. Shaker flask cultures were co-transfected with a mixture of pTT/SEAP:pEGFP (9:1) plasmids (pEGFP was added to monitor for transfection efficiency). With both linear and branched PEI, SEAP accumulated in the culture medium for up to 96 hours post-transfection (hpt) (FIG. 4), but gene transfer and expression level were 50% higher using the linear isoform. These results clearly demonstrate that linear, and to a lesser extent branched PEI are effective for gene transfer in suspension-growing cells. In addition, SEAP expression levels obtained with suspension-growing cells using linear PEI were comparable with those obtained with adherent-growing cells. For all experiments discussed below, only linear PEI was used.

In order to design a robust, simple and scalable transfection process, two steps had to be simplified: the 3 hrs incubation of DNA-PEI complexes with cells in a reduced culture volume, and the medium change 3 hrs prior to transfection. The first step was performed with the assumption that it would promote interaction of the DNA-PEI complexes with the cells and thus increase transfection efficiency. The second was done according to reports showing deleterious effect of conditioned medium on transfection efficiency (Schlaeger E-J. et al., *Cytotechnology*, 30, 71-83 (1999); Ruponen M. et al., *Biochim. Biophys. Acta*, 1415, 331-341 (1999)). Whereas medium exchange is simple to perform on a small scale, this step represents a significant hurdle at scales greater than a few liters.

The effect of cell density at the time of transfection was first evaluated (FIG. 5A) by transfecting high density (hatched bars; 10 ml at $1 \times 10^6$ cells $ml^{-1}$) or low density cultures (gray bars; 20 ml at $2.5 \times 10^5$ cells $ml^{-1}$) in shaker flasks. Three hours later, the high cell density flask was diluted to $5 \times 10^5$ cells $ml^{-1}$ with fresh medium, and GFP expression monitored 72 hrs later. This experiment showed that cell concentrations prior to transfection could be omitted, as only a slight decrease (<10%) in transfection efficiency and a 15% decrease in GFP expression level was observed when cells were transfected in a larger culture volume.

Figure 5:
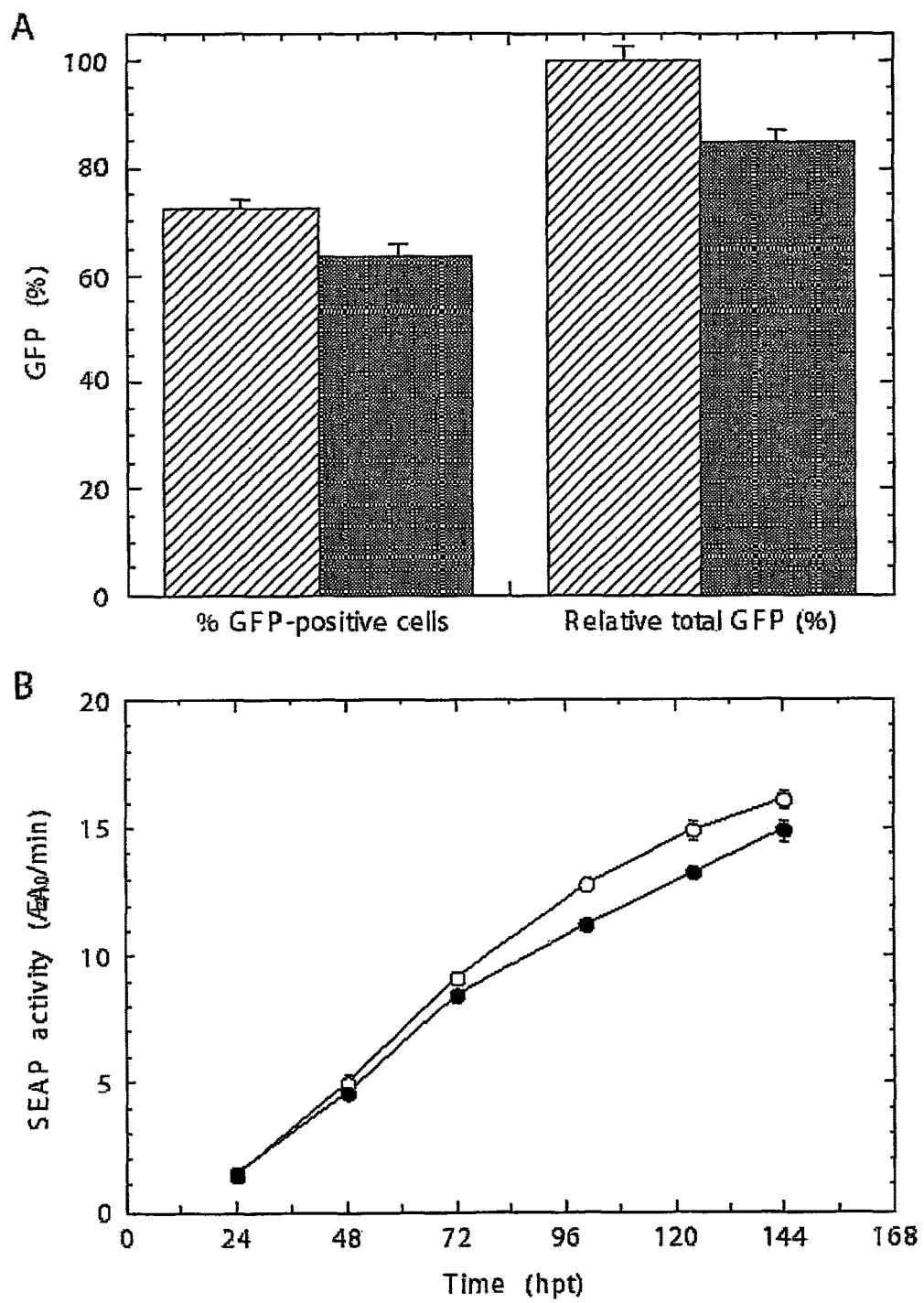
FIG. 5 is a graph showing effects of cell density and of conditioned medium. (A) Transfection efficiency and relative total GFP expression (in percent) obtained following transfection using standard conditions (hatched bars: 10 ml of cells at $1 \times 10^6\ ml^{-1}$ followed by addition of 10 ml of fresh medium 3 h after transfection) or using cells at $5 \times 10^5\ ml^{-1}$ in 20 ml of culture medium (gray bars). GFP was monitored 72 hpt. Relative total GFP was obtained following multiplication of percent GFP-positive cells by the mean fluorescence intensity. (B) Cells were seeded in 20 ml of 1% BCS-supplemented HSFM at a density $2.5 \times 10^5\ ml^{-1}$ 24 h before transfection. The medium was then left unchanged (conditioned: open circles) or replaced with 20 ml of fresh medium (closed circles). Three hours later, cells were transfected by the addition of 2 ml of DNA-PEI complexes (20 µg of pTT/SEAP and 40 µg of linear PEI).

The next evaluated was the effect of conditioned medium on SEAP expression using suspension growing cells. For this study, cells were seeded in shaker flasks at a density of $2.5 \times 10^5$ cells $ml^{-1}$. Twenty-four hours later, transfection was performed with or without a complete medium exchange. As shown in FIG. 5B, no significant difference in SEAP expression was observed when the transfection was carried out in medium conditioned for 24 hrs, indicating that medium exchange is not necessary.

Transfection in Bioreactors

To demonstrate the scalability of the process, a 3.5-l bioreactor culture was transfected with a mixture of pTT/SEAP:pEGFP plasmids (19:1). One hour later, a sample (25 ml) was withdrawn and transferred into a shaker flask as a control. In the bioreactor (FIG. 13A, solid lines), SEAP (circles) accumulated up to 144 hpt and then reached a plateau, whereas accumulation continued up to 216 hpt in the control shaker flask (dashed lines). The percentage of GFP-positive cells (squares) at 96 hpt reached 54 and 50% for the bioreactor and the shaker flask, respectively. At the end of the culture, cell density was 4.1 and $4.7 \times 10^6$ cells $ml^{-1}$ with a viability of 62 and 72% for the bioreactor and the shaker flask, respectively (FIG. 13B). Although viable cell density was 25% lower in the bioreactor compared with the shaker flask, volumetric SEAP productivity was almost 2-fold higher. Similar results were systematically observed in five independent experiments (results not shown), indicating that the productivity of secreted proteins might be increased when using a controlled environment.

Purification of SEAP and Production of Other r-Proteins

Purification of Myc-(His)$_6$-tagged SEAP harvested from the bioreactor run (FIG. 13) by immobilized metal affinity chromatography (IMAC) is shown in FIG. 14A. The left panel shows Coomassie blue-stained protein pattern from the culture medium before loading on the column (lane 1), flow-through (lane 2) and eluted material using 150 mM imidazole (lane 3). The right panel shows immunodetection of SEAP in the same fractions using anti-Myc antibody. This figure shows that all of the His-tagged SEAP was retained on the column, whereas very few, if any, serum protein bound to it (SEAP migrates with an apparent molecular weight slightly higher than BSA). SEAP quantification in the eluted fraction using the Lowry protein assay showed that ~60 mg of His-tagged SEAP could be recovered by IMAC from the 3-l bioreactor culture. As shown in FIG. 14B, high expression levels in bioreactor were also obtained with other secreted r-proteins. Fourteen- (lanes 1, 3 and 4) or 3.5-liter (lane 2) bioreactors were transfected with pTT plasmids encoding for Neurophilin-1 and VEGF (1:1 ratio, lane 1), Tie2 (lane 2), Cripto (lane 3) and c-Met (lane 4). All cultures were harvested 5 days post-transfection. With the exception of Cripto, which has been reported highly glycosylated on serine, threonine and asparagine (Schiffer S. G. et al., J. Biol. Chem., 276, 37769-37778 (2001) 22), glycosylation of the expressed proteins appeared to be relatively homogenous, as suggested by their migration behaviour following SDS-PAGE. High expression levels of intracellular r-proteins were also obtained as shown in FIG. 14C. In this experiment, 293E cells were transfected with pTT plasmids encod ing for sgGFP (lane 1), herpes simplex virus ribonucleotide reductase (RR1, lane 2), mouse $G_{\alpha q}$ (lane 5), human p27$^{Kip1}$ (lane 6), yeast pyruvate carboxylase (PYC, lane 7), adenovirus E1B$^{19K}$ (lane 8), human hexokinase 1 (HK, lane 9) and human glucokinase (GK, lane 10). Three days after transfection, cells were rinsed with PBS, solubilized in sample buffer (GFP, RR1 and $G_{\alpha q}$) or extracted with lysis buffer (p27$^{Kip1}$, PYC, E1B$^{19K}$, HK and GK), and proteins analyzed by SDS-PAGE. Quantification of r-proteins shown in FIG. 14 is summarized in Table 1.

TABLE 1

Summary of r-protein expression level

| r-Protein | Tag | Localization | Culture mode | Concentration (mg/l) |
|---|---|---|---|---|
| Human SEAP | Myc-(His)$_6$ | Secreted | 3-l bioreactor | 20$^a$ |
| Human Neuropilin-1 | Myc-(His)$_6$ | Secreted | 14-l bioreactor | 8$^b$ |
| Human VEGF | Myc-(His)$_6$ | Secreted | 14-l bioreactor | 10$^b$ |
| Human Tie2 | Myc-(His)$_6$ | Secreted | 3-l bioreactor | 9 |
| Human Cripto | Myc-(His)$_6$ | Secreted | 14-l bioreactor | 9 |
| Human c-Met | Myc-(His)$_6$ | Secreted | 14-l bioreactor | 1 |
| sgGFP | None | Intracellular | Shaker flask | 20 |
| Herpes virus RR1 | None | Intracellular | Shaker flask | 50 |
| Mouse G$\alpha_q$ | None | Membrane | T-flask | 16 |
| Human p27$^{Kip1}$ | None | Intracellular | T-flask | 14 |
| Human hexokinase | None | Intracellular | Shaker flask | 40 |
| Human glucokinase | None | Intracellular | Shaker flask | 30 |
| Yeast PYC | None | Intracellular | 1-l bioreactor | 4 |
| Adenovirus E1B$^{19K}$ | None | Intracellular | T-flask | 3 |

$^a$After purification by IMAC
$^b$Neurophilin-1 and VEGF were co-transfected

In the case of RR1, volumetric production was 50 mg/l, representing 20% of total cell protein (TCP). The mouse G$\alpha_q$ was expressed at 16 mg/l, compared with a barely detectable level (by Coomassie staining) when expressed from pcDNA3.1 vector (lane 4).

Although various particular embodiments of the present invention have been described hereinbefore for purposes of illustration, it would be apparent to those skilled in the art that numerous variations may be made thereto without departing from the spirit and scope of the invention, as defined in the appended claims.

What is claimed is:

1. A human kidney cell line designated 293SFE and deposited under IDAC Accession No. 020502.

2. An expression vector for expression of a recombinant protein, said vector comprising a first DNA sequence encoding the recombinant protein, said first DNA sequence being under control of a CMV5 promoter, said expression vector further comprising a second DNA sequence, wherein the second DNA sequence comprises the nucleotide sequence as set forth in SEQ ID NO: 1 or a fragment thereof containing 9 to 20 EBNA1 binding sites, the EBNA1 binding sites selected from the group consisting of nucleotides 36-53 of SEQ ID NO:1, nucleotides 66-83 of SEQ ID NO:1, nucleotides 126-143 of SEQ ID NO:1, nucleotides 276-293 of SEQ ID NO:1 and nucleotides 302-319 of SEQ ID NO:1; the second DNA sequence is located 3' to the CMV5-promoter; and the second DNA sequence enhances transcriptional activity of the promoter and transient expression of the recombinant protein when present in a cell expressing EBNA1 protein, wherein the vector minus the first DNA sequence is selected from the group consisting of pTT, pTT (delta DS), pTTm, pTTn, pTTo, pTT4a, and pTT4c.

3. A process for preparing recombinant human kidney 293 cells, the process comprising transfecting host human kidney 293 cells with the expression vector of claim 2.

4. The process of claim 3, which is carried out in the presence of polyethylenimine (PEI) as a transfection reagent.

5. The process of claim 4 wherein the PEI is a linear PEI or a branched PEI.

6. The process of claim 5, wherein the average molecular weight of the PEI is from about 10 to about 100 kDa.

7. The process of claim 6, wherein the average molecular weight of the PEI is about 25 kDa.

8. The process of claim 5, wherein the transfecting step is not adenovirus-mediated.

9. The process of claim 3, wherein the host human kidney cells are human kidney 293 cells modified to stably express EBNA1 protein.

10. An expression vector selected from the group consisting of pTT, pTT (delta DS), pTTm, pTTn, pTTo, pTT4a, pTT4c, and a variant of pTT; the variant of pTT comprising a fragment of the oriP region of pTT, the fragment of the oriP region comprising 9 to 20 EBNA1 binding sites selected from the group consisting of nucleotides 36-53 of SEQ ID NO:1, nucleotides 66-83 of SEQ ID NO:1, nucleotides 126-143 of SEQ ID NO:1, nucleotides 276-293 of SEQ ID NO:1 and nucleotides 302-319 of SEQ ID NO:1.

11. The expression vector of claim 10, wherein the expression vector is pTT.

* * * * *

SEQUENCE LISTING

<160> NUMBER OF SEQ ID NOS: 1

<210> SEQ ID NO 1
<211> LENGTH: 623
<212> TYPE: DNA
<213> ORGANISM: Epstein-Barr Virus

<400> SEQUENCE: 1

```
caagaattct catgtttgac agcttatcat cgtgaggata gcatatgcta cccggataca      60
gattaggata gcatatacta cccagatata gattaggata gcatatgcta cccagatata     120
gattaggata gcctatgcta cccagatata aattaggata gcatatacta cccagatata     180
gattaggata gcatatgcta cccagatata gattaggata gcctatgcta cccagatata     240
gattaggata gcatatgcta cccagatata gattaggata gcatatgcta tccagatatt     300
tgggtagtat atgctaccca gatataaatt aggatagcat atactaccct aatctctatt     360
aggatagcat atgctacccg gatacagatt aggatagcat atactaccca gatatagatt     420
aggatagcat atgctaccca gatatagatt aggatagcct atgctaccca gatataaatt     480
aggatagcat atactaccca gatatagatt aggatagcat atgctaccca gatatagatt     540
aggatagcct atgctaccca gatatagatt aggatagcat atgctatcca gatatttggg     600
tagtatatgc tacccatggc aac                                             623
```